US012790284B2

(12) United States Patent
Taggert et al.

(10) Patent No.: US 12,790,284 B2
(45) Date of Patent: Nov. 10, 2026

(54) NITRIFICATION INHIBITORS

(71) Applicant: The University of Melbourne, Melbourne (AU)

(72) Inventors: Bethany Isabel Taggert, Melbourne (AU); Uta Wille, Melbourne (AU); Deli Chen, Melbourne (AU)

(73) Assignee: The University of Melbourne, Melbourne (AU)

( * ) Notice: Subject to any disclaimer, the term of this patent is extended or adjusted under 35 U.S.C. 154(b) by 1034 days.

(21) Appl. No.: 17/753,474

(22) PCT Filed: Sep. 4, 2020

(86) PCT No.: PCT/AU2020/050929
§ 371 (c)(1),
(2) Date: Mar. 3, 2022

(87) PCT Pub. No.: WO2021/042169
PCT Pub. Date: Mar. 11, 2021

(65) Prior Publication Data

US 2022/0324770 A1 Oct. 13, 2022

(30) Foreign Application Priority Data

Sep. 5, 2019 (AU) ................................ 2019903269

(51) Int. Cl.
*C05G 3/90* (2020.01)
*C05G 5/12* (2020.01)
*C07D 249/04* (2006.01)

(52) U.S. Cl.
CPC ................. *C05G 3/90* (2020.02); *C05G 5/12* (2020.02); *C07D 249/04* (2013.01)

(58) Field of Classification Search
CPC ........... C05G 3/90; C05G 5/12; C07D 249/04
See application file for complete search history.

(56) References Cited

U.S. PATENT DOCUMENTS 9,176,380 B2 11/2015 Bowman et al.
10,030,027 B2 7/2018 Berger et al.
(Continued)

FOREIGN PATENT DOCUMENTS

BR 102012023741 A2 10/2014
CA 2182011 C 6/2001
(Continued)

OTHER PUBLICATIONS

Kale et al., "Conventional and microwave-assisted multicomponent reaction of alkyne, halide and socium azide catalyzed by copper apatite as heterogeneous base and catalyst in water", Current Chemistry Letters (2012), 1(2), 69-80.
(Continued)

*Primary Examiner* — Jennifer A Smith
(74) *Attorney, Agent, or Firm* — Dorsey & Whitney LLP

(57) ABSTRACT

The present invention generally relates to nitrification inhibitors and compositions comprising nitrification inhibitors. The present invention also relates to use of the nitrification inhibitors and compositions for application to fertilisers, plants, agricultural areas (e.g. soils or pastures) to reduce or inhibit the oxidation of ammonium nitrogen to nitrite and nitrate nitrogen, such as the oxidation of ammonia- or urea-based fertilisers.

4 Claims, 7 Drawing Sheets

(56) References Cited

U.S. PATENT DOCUMENTS

2013/0315874 A1* 11/2013 Melander .............. A01N 63/40
514/397
2015/0348778 A1 12/2015 Shimizu et al.

FOREIGN PATENT DOCUMENTS

| | | | |
|---|---|---|---|
| CN | 108976214 | A | 12/2018 |
| EA | 002098 | B1 | 12/2001 |
| RU | 2647924 | C1 | 3/2018 |
| WO | 2008144223 | A2 | 11/2008 |
| WO | 2010077603 | A1 | 7/2010 |
| WO | 2012074931 | A2 | 6/2012 |
| WO | 2014140310 | A1 | 9/2014 |
| WO | 2016183118 | A1 | 11/2016 |

OTHER PUBLICATIONS

Kale et al., Magnetically recyclable nanoparticles for the cycloaddition reaction of alkynes, halides and azides in aqueous media, RSC Advances (2013), 3(22), 8184-8192.
Khan et al., "Versatile Synthesis of 1, 2, 3-Triazolium-based Ionic Liquids", ARKIVOC 2009 (xii) 193-208; Synthesis (2009), (23), 3975-3982.
Lartey et al., "Branched isomeric 1, 2, 3-triazolium-based ionic liquids: new insight into structure-property relationships", Phys. Chem. Chem. Phys., 2015, 17, 29834-29843.
Pretorius et al., "Synthesis and catalytic applications of 1, 2, 3-triazolylidene gold(I) complexes in silver-free oxazoline syntheses and C—H bond activation", Dalton Transactions (2016), 45(37), 14591-14602.
Pretorius et al., "Synthesis, hemilability, and catalytic transfer hydrogen activity of iridium (III) and ruthenium (II) complexes containing oxygen-functionalised triazolylidene ligands", Journal of Organometallic Chemistry (2017), 845, 196-205.
Pyta et al., "Synthesis, structure, and antimicrobial evaluation of a new gossypol triazole conjugates functionalized with aliphatic chains and benzyloxy groups", Bioorganic & Medicinal Chemistry Letters (2016), 26(17), 4322-4326.
Wen et al., "Synthesis and Bioactivity of Novel Trisubstituted Triazole Nucleosides", Nucleosides, Nucleotides and Nucleic Acids 2016, vol. 35, No. 3, 147-160.
CAS Registry No. 1856615-32-1, 01.02.2016.
CAS Registry No. 2140428-99-6, 10.11.2017.
Labadie, Guillermo R. et al., "Targeting tuberculosis through a small focused library of 1,2,3-triazoles", Springer Science+ Business Media B.V., Jun. 2, 2011.
PubChem CID: 104093357, Create Date: Jan. 13, 2016, methyl 2-[4-(3-hydroxypropyl)-1H-1,2,3-triazol-1-yl]acetate.
PubChem CID: 132370201, Create Date: Mar. 2, 2018, Methyl 2-(4-(3-aminopropyl)-1H-1,2,3-triazol-1-yl)acetate dihydrochloride.
PubChem CID: 132370202, Create Date: Mar. 2, 2018, methyl 2-[4-(3-aminopropyl)-1H-1,2,3-triazol-1-yl]acetate.
PubChem CID: 67741877, Create Date: Nov. 30, 2012, Methyl 2-(4-ethyltriazol-1-yl)acetate.
PubChem CID: 89447039, Create Date: Feb. 13, 2015, Ethyl 2-(4-ethyltriazol-1-yl)acetate.
Russian Search Report dated Feb. 9, 2024 issued in Russian patent application No. 2022105585/04.
Sabbah et al., "Synthesis and biological evaluation of new N-acyl-homoserine-lactone analogues, based on triazole and tetrazole scaffolds, acting as LuxR-dependent quorum sensing modulators", Bioorganic & Medicinal Chemistry, 2012, 20, p. 4727-4736.
CAS Registry No. 2302762-84-9; STN Entry Date Apr. 7, 2019; 4-Methyl-N-2-propyn-1-yl-1H-1,2,3-triazole-1-ethanamine.
Karlsson, S. et al., 'Development of a Safe Continuous Manufacturing Route to 2 (4-Isopropyl 1H 1,2,3-triazol-1-yl) acetic Acid', Org. Process Res. Dev. 2017, vol. 21, 1668-1674.
Moghaddam, F. et al., 'Cobalt-Copper Ferrite Nanoparticles Catalyzed Click Reaction at Room-Temperature: Green Access to 1,2,3-Triazole Derivatives', ChemistrySelect 2018, vol. 3, pp. 2586-2593.
Raiguel, S. et al., 'Multi-Gram Scale Synthesis of 1,2,3-Triazolium Ionic Liquids and Assay of Their Resistance towards Bases', Eur. J. Org. Chem. 2018, vol. 35, pp. 4850-4856.
Simone et al., "Structure Based Discovery of Inhibitors of Microsomal Prostaglandin E2 Synthase 1,5 Lipoxygenase and 5 Lipoxygenase Activitating Protein: Promising Hits for the Development of New Anti-inflammatory Agents", J. Med. Chem., vol. 54, pp. 1565 1575.
Yan, F. et al., 'Toward a Materials Genome Approach for Ionic Liquids: Synthesis Guided by Ab Initio Property Maps', J. Phys. Chem. B 2014, vol. 118, pp. 13609-13620.
CAS Registry No. 1426684-80-1; STN Entry Date Mar. 29, 2013; 6-(4-Butyl-1H-1,2,3-triazol-1-yl)Hexyl 2- methyl-2-propenoate [3], Mar. 29, 2023.
CAS Registry No. 1396338-45-6; STN Entry Date Sep. 26, 2012; 4-Butyl-1-ethynyl-1H-1,2,3-triazole [3], Sep. 26, 2012.
Beck , et al., "Discovery of Molidustat (BAY 85-3934): A Small-Molecule Oral HIF-Prolyl Hudroxylase (HIF-PH) Inhibitor for the Treatment of Renal Anemia", ChemMedChem, vol. 13, 2018, 988-1003.
Clave , et al., "Ecological Recycling of a Bio-Based Catalyst for Cu Click Reaction: A New Strategy for a Greener Sustainable Catalysis", ChemistrySelect, vol. 1, 2016, 1410-1416.
Doohyun , et al., "Efficient Syntheses of 1,2,3-Triazoloamide Derivatives Using Solid- and Solution-Phase Synthetic Approaches", Molecules, vol. 20, 2015, 19984-20013.
Kimber , et al., "Synthesis of coper Catalysts for Click Chemistry from Distillery Wastewater Using Magnetically Recoverable Bionanoparticles", Green Chemistry, vol. 21, 2019, 4020-4024.
Nulwala, et al., "N-Vinyltriazoles: A New Functional Monomer Family Through Click Chemistry", Macromolecules, vol. 43, 2010, 5474-5477.
Obadia , et al., "Poly(Vinyl Ester 1,2,3-Triazolium)s: A New Member of the Poly(Ionic Liquid)s Family", Chem. Commun., vol. 51, 2015, 3332-3335.
CAS Registry No. 1707375-48-1; STN Entry Date May 19, 2015; Methyl 1-(2-propyn-1-yl)-1H-1,2,3- triazole-4-acetate.
CAS Registry No. 1855114-60-1; STN Entry Date Jan. 29, 2016; 2-[3-[4-(2-aminoethyl)-IH-1,2,3-triazol-I-yl]-2,2-dimethylpropyl]-IH-Isoindole-1 ,3(2H)-dione.
CAS Registry No. 1856615-32-1; STN Entry Date Feb. 1, 2016; 2-[3-[4-(I-aminobutyl)-I H-1 ,2,3-triazol-I-yl]-2,2-dimethylpropyl]-IH-Isoindole-1 ,3(2H)-dione.
CAS Registry No. 1871295-32-7; STN Entry Date Feb. 21, 2016; 2-[2-[4-(diethoxymethyl)-IH-1,2,3-triazol- I-yl] ethyl]-IH-Isoindole-I,3(2H)-dione.
CAS Registry No. 2098027-72-4; STN Entry Date Jun. 8, 2017; 4-Ethyl-5-methyl-1-(2-propyn-1-yl)-1H-1,2,3-triazole.
CAS Registry No. 2140428-00-6; STN Entry Date Nov. 10, 2017; 2-[3-[4-(2-amino-3-hydroxypropyl)-IH-1,2,3-triazol-I-yl]-2-hydroxypropyl]-IH-Isoindole-I,3(2H)-dione.
CAS Registry No. 2155710-90-8; STN Entry Date Dec. 11, 2017; 2-[3-[4-(2-amino-3-methoxypropyl)-IH-1,2,3-triazol-I-yl]-2-hydroxypropyl]-IH-Isoindole-I,3(2H)-dione.
CAS Registry No. 2323221-31-2; STN Entry Date Jun. 3, 2019; 1-(4,4-Dimethyl-2-pentyn-1-yl)-4-methyl-1H-1,2,3-triazole.
Fletcher, J. T. et al., '1-allyl- and 1-benzyl-3-methyl-1,2,3-triazolium salts via tandem click transformations', Synthesis. 2010, vol. 19, pp. 3339-3345.
Ghiano, D. G. et al., 'Antitubercular activity of 1,2,3-triazolyl fatty acid derivatives', European Journal of Medicinal Chemistry. 2017, vol. 125, pp. 842-852.
International Search Report and Written Opinion dated Nov. 18, 2020 received in international patent application No. PCT/AU2020/050929.
Kamijo, S et al., Four-component coupling reactions of silylacetylenes, allyl carbonates, and trimethylsilyl azide catalyzed by a Pd(0)—Cu(I) bimetallic catalyst. Fully substituted triazole synthesis, Tetrahedron Letters. 2004, vol. 45, pp. 689-691.

(56) References Cited

OTHER PUBLICATIONS

Keunchan, O. et al., 'A convergent synthesis of new β-turn mimics by click chemistry', Chemical Communications. 2006, vol. 29, pp. 3069-3071.
Porta, E. O. J. et al., 'Antitrypanosomal and antileishmanial activity of prenyl-1,2,3-triazoles', MedChemComm. 2017, vol. 8(5), pp. 1015-1021.

* cited by examiner

NITRIFICATION INHIBITORS

FIELD OF THE INVENTION

The present invention generally relates to nitrification inhibitors and compositions comprising nitrification inhibitors. The present invention also relates to use of the nitrification inhibitors and compositions for application to fertilisers, plants, agricultural areas (e.g. soils or pastures) to reduce or inhibit the oxidation of ammonium nitrogen to nitrite and nitrate nitrogen, such as the oxidation of ammonia- or urea-based fertilisers.

BACKGROUND OF THE INVENTION

High application of nitrogen fertilisers is common in agricultural systems to achieve optimal yields. However, this practice results in the release of reactive nitrogen species into the surrounding environments due to notoriously low nitrogen use efficiencies (NUEs). Plants rarely assimilate more than 50% of applied fertiliser nitrogen. In Australia, NUEs fall anywhere between 6 and 59% depending on crop type; globally NUEs have remained around 50% since the 1980's (Chen, D., et al., *Australian Journal of Soil Research,* 2008, 46, 289-301; Rowlings, A. W., et al., *Agriculture, Ecosystems and Environment,* 2016, 216, 216-225). The remaining nitrogen is vulnerable to be lost from the plant/soil system via ammonia ($NH_3$) volatilisation, nitrate ($NO_3^-$) leaching and gaseous emissions resulting from denitrification.

Of pertinent concern are losses resulting in the release of nitrous oxide ($N_2O$), a global warming agent 300 times more potent than carbon dioxide ($CO_2$), which also catalyses the destruction of stratospheric ozone. Atmospheric $N_2O$ concentrations have increased at a rate of 0.73 ppb per year for the past three decades, and the use of nitrogen fertilisers is a leading contributor (Ciais, P., et al., Carbon and Other Biogeochemical Cycles. In: Climate Change 2013: The Physical Science Basis. Contribution of Working Group I to the Fifth Assessment Report of the Intergovernmental Panel on Climate Change, Cambridge University Press, Cambridge, United Kingdom and New York, NY, USA).

Ammonium ($NH_4^+$) in soils, either directly applied or arising indirectly from microbial conversion of nitrogen fertilisers, is quickly oxidised to nitrite ($NO_2^-$) and then $NO_3^-$ through the nitrification process. $NO_3^-$ is subsequently subjected to denitrification, where it is sequentially reduced to $NO_2^-$, nitric oxide (NO), $N_2O$ and finally $N_2$. Soils with high $NO_3^-$ content are at risk of nitrogen loss via leaching of $NO_3^-$ itself, or through gaseous losses of NO and $N_2O$ arising from incomplete denitrification. Reducing instances of high $NO_3^-$ concentration in soils is therefore desirable to mitigate these losses.

Slowing the conversion of $NH_4^+$ to $NO_3^-$ using fertilisers amended with nitrification inhibitors is a strategy to increase NUE. Nitrification inhibitors inhibit nitrifying microbes in the soil, increasing the residence time of $NH_4^+$ and decreasing nitrogen losses from leaching ($NO_3^-$) and denitrification ($N_2O$, $NO_x$, $N_2$). The use of nitrification inhibitors is also recommended by the Intergovernmental Panel on Climate Change (IPCC) to mitigate $N_2O$ emissions. Of the many compounds identified as nitrification inhibitors, the most widely researched commercial products are based on one of three chemicals: dicyandiamide (DCD, AlzChem AG), 2-chloro-6-(trichloromethyl)-pyridine (Nitrapyrin or N-Serve, Dow Chemical Co.) and 3,4-dimethylpyrazole phosphate (DMPP or ENTEC, BASF AG; the active compound is 3,4-dimethylpyrazole (DMP)). The effectiveness of these inhibitors varies greatly and appears to be influenced by environmental conditions and soil characteristics, such as pH, water content/rainfall, temperature and soil type.

DMPP is often identified as one of the more promising nitrification inhibitor candidates as it has undergone extensive toxicological testing, is effective at low concentrations and has low mobility in soils due to its positive charge (Zerulla, W., et al., *Biology and Fertility of Soils,* 2001, 34, 79-84). Whilst being the most promising inhibitor to date, DMPP has been found to have vastly different inhibitory activity in field studies for reducing leaching and $N_2O$ emissions—ranging from no effect to as high as 70% inhibition for reasons not yet well understood. DMPP has shown little to no impact on improving crop/biomass yields and thus economically is not an attractive option to farmers, who ideally would offset the higher expense of the fertiliser with increased yields.

DMPP inhibitory activity is also known to be inversely related to temperature, with significant decreases in activity observed over relatively small temperature windows. Studies have shown that at a temperature of 35° C. DMPP remains effective for only one week (Mahmood, T., et al., *Soil Research,* 2017, 55, 715-722).

It has also been reported that low pH soil conditions severely reduce DMPP activity, potentially due to the switch from the autotrophic bacteria that DMPP targets to heterotrophic bacteria predominating under these acidic conditions (Barth, G., et al., *Biology and Fertility of Soils,* 2001, 34, 98-102; Xi, R., et al., *AMB Express,* 2017, 7, 129). Attempts to circumvent some of these issues have included the reformulation of the active 3,4-dimethylpyrazole (DMP) core with succinic acid to create the isomeric mixture of 2-(N-3,4-dimethylpyrazole)succinic acid and 2-(N-4,5-dimethylpyrazole)succinic acid referred to as DMPSA. DMPSA is believed to be metabolised to the active DMP core once applied to soils, resulting in a longer lifetime in soils.

Accordingly, there exists a need to develop new nitrification inhibitors to address the above-mentioned shortcomings.

SUMMARY OF THE INVENTION

The present invention is predicated on the discovery that substituted 1,2,3-triazoles are effective nitrification inhibitors of low volatility.

Accordingly, in one aspect the present invention provides a method for reducing nitrification in soil comprising treating the soil with a compound of Formula (I):

(I)

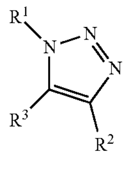

wherein $R^1$ and $R^2$ are independently selected from optionally substituted —$C_1$-$C_{10}$alkyl, —$C_2$-$C_{10}$alkenyl, —$C_2$-$C_{10}$alkynyl, —$C_1$-$C_{10}$alkylC(O)OR$^4$, —$C_2$-$C_{10}$alkenylC(O)OR$^4$, —$C_2$-$C_{10}$alkynylC(O)OR$^4$, —$C_1$-$C_{10}$alkylOC(O)R$^4$, —$C_2$-$C_{10}$alkenylOC(O)R$^4$, —$C_2$-$C_{10}$alkynylOC(O)R$^4$, —$C_1$-$C_{10}$alkylOC(O)OR$^4$, —$C_2$-$C_{10}$alkenylOC(O)OR$^4$, —$C_2$-$C_{10}$alkynylOC(O)

$OR^4$, —$C_1$-$C_{10}$alkylC(O)N($R^5R^6$), —$C_2$-$C_{10}$alkenylC(O)N($R^5R^6$), —$C_2$-$C_{10}$alkynylC(O)N($R^5R^6$), —$C_1$-$C_{10}$alkylNR$^5$C(O)$R^6$, —$C_2$-$C_{10}$alkenylNR$^5$C(O)$R^6$ and —$C_2$-$C_{10}$alkynylNR$^5$C(O)$R^6$;

$R^3$ is H or is selected from optionally substituted —$C_1$-$C_{10}$alkyl, —$C_2$-$C_{10}$alkenyl, —$C_2$-$C_{10}$alkynyl, —$C_1$-$C_{10}$alkylC(O)$OR^4$, —$C_2$-$C_{10}$alkenylC(O)$OR^4$, —$C_2$-$C_{10}$alkynylC(O)$OR^4$, —$C_1$-$C_{10}$alkylOC(O)$R^4$, —$C_2$-$C_{10}$alkenylOC(O)$R^4$, —$C_2$-$C_{10}$alkynylOC(O)$R^4$, —$C_1$-$C_{10}$alkylOC(O)$OR^4$, —$C_2$-$C_{10}$alkenylOC(O)$OR^4$, —$C_2$-$C_{10}$alkynylOC(O)$OR^4$, —$C_1$-$C_{10}$alkylC(O)N($R^5R^6$), —$C_2$-$C_{10}$alkenylC(O)N($R^5R^6$), —$C_2$-$C_{10}$alkynylC(O)N($R^5R^6$), —$C_1$-$C_{10}$alkylNR$^5$C(O)$R^6$, —$C_2$-$C_{10}$alkenylNR$^5$C(O)$R^6$ and —$C_2$-$C_{10}$alkynylNR$^5$C(O)$R^6$;

$R^4$ is selected from —$C_1$-$C_4$alkyl, —$C_2$-$C_4$alkenyl and —$C_2$-$C_4$alkynyl; and $R^5$ and $R^6$ are independently selected from H, —$C_1$-$C_4$alkyl, —$C_2$-$C_4$alkenyl and —$C_2$-$C_4$alkynyl;

or agriculturally acceptable salts thereof.

In another aspect, the present invention provides a composition for reducing nitrification comprising a compound of Formula (I) as defined above and at least one agriculturally acceptable adjuvant or diluent.

In a further aspect, the present invention provides a fertiliser comprising a urea- or ammonium-based fertiliser and a compound of Formula (I) as defined herein.

In yet another aspect, the present invention provides a compound of Formula (II):

(II)

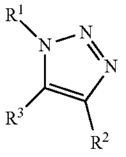

wherein $R^1$ and $R^2$ are independently selected from optionally substituted —$C_1$-$C_{10}$alkyl, —$C_2$-$C_{10}$alkenyl, —$C_2$-$C_{10}$alkynyl, —$C_1$-$C_{10}$alkylC(O)$OR^4$, —$C_2$-$C_{10}$alkenylC(O)$OR^4$, —$C_2$-$C_{10}$alkynylC(O)$OR^4$, —$C_1$-$C_{10}$alkylOC(O)$R^4$, —$C_2$-$C_{10}$alkenylOC(O)$R^4$, —$C_2$-$C_{10}$alkynylOC(O)$R^4$, —$C_1$-$C_{10}$alkylOC(O)$OR^4$, —$C_2$-$C_{10}$alkenylOC(O)$OR^4$, —$C_2$-$C_{10}$alkynylOC(O)$OR^4$, —$C_1$-$C_{10}$alkylC(O)N($R^5R^6$), —$C_2$-$C_{10}$alkenylC(O)N($R^5R^6$), —$C_2$-$C_{10}$alkynylC(O)N($R^5R^6$), —$C_1$-$C_{10}$alkylNR$^5$C(O)$R^6$, —$C_2$-$C_{10}$alkenylNR$^5$C(O)$R^6$ and —$C_2$-$C_{10}$alkynylNR$^5$C(O)$R^6$;

$R^3$ is H or is selected from optionally substituted —$C_1$-$C_{10}$alkyl, —$C_2$-$C_{10}$alkenyl, —$C_2$-$C_{10}$alkynyl, —$C_1$-$C_{10}$alkylC(O)$OR^4$, —$C_2$-$C_{10}$alkenylC(O)$OR^4$, —$C_2$-$C_{10}$alkynylC(O)$OR^4$, —$C_1$-$C_{10}$alkylOC(O)$R^4$, —$C_2$-$C_{10}$alkenylOC(O)$R^4$, —$C_2$-$C_{10}$alkynylOC(O)$R^4$, —$C_1$-$C_{10}$alkylOC(O)$OR^4$, —$C_2$-$C_{10}$alkenylOC(O)$OR^4$, —$C_2$-$C_{10}$alkynylOC(O)$OR^4$, —$C_1$-$C_{10}$alkylC(O)N($R^5R^6$), —$C_2$-$C_{10}$alkenylC(O)N($R^5R^6$), —$C_2$-$C_{10}$alkynylC(O)N($R^5R^6$), —$C_1$-$C_{10}$alkylNR$^5$C(O)$R^6$, —$C_2$-$C_{10}$alkenylNR$^5$C(O)$R^6$ and —$C_2$-$C_{10}$alkynylNR$^5$C(O)$R^6$;

$R^4$ is selected from —$C_2$-$C_4$alkyl, —$C_2$-$C_4$alkenyl and —$C_2$-$C_4$alkynyl; and $R^5$ and $R^6$ are independently selected from H, —$C_1$-$C_4$alkyl, —$C_2$-$C_4$alkenyl and —$C_2$-$C_4$alkynyl;

provided that the compound is not:

1-butyl-4-pentyl-1H-1,2,3-triazole;

1,4-butyl-1H-1,2,3-triazole;

4-butyl-1H-1,2,3-triazole-1-acetic acid ethyl ester;

1-butyl-4-(α,α-dimethyl methanol)-1H-1,2,3-triazole;

4-butyl-1H-1,2,3-triazole-1-propanamine;

ethyl 4,5-bis(hydroxymethyl)-1H-1,2,3-triazole-1-acetate; or 1,4-dipropyl-1H-1,2,3-triazole;

or agriculturally acceptable salts thereof.

In a further aspect the present invention provides a compound of the Formula (IIa):

(IIa)

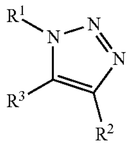

wherein $R^1$ is —$C_1$-$C_{10}$alkyl substituted with one or more hydroxy, —$C_1$-$C_4$alkoxy- or 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino; or $R^1$ is selected from —$C_2$-$C_{10}$alkenyl, —$C_2$-$C_{10}$alkynyl, —$C_2$-$C_{10}$alkylC(O)O$C_1$-$C_4$alkyl, —$C_1$-$C_{10}$alkylC(O)O$C_2$-$C_4$alkenyl, —$C_1$-$C_{10}$alkylC(O)O$C_2$-$C_4$alkynyl, —$C_2$-$C_{10}$alkenylC(O)$OR^4$, —$C_2$-$C_{10}$alkynylC(O)$OR^4$, —$C_1$-$C_{10}$alkylOC(O)$R^4$, —$C_2$-$C_{10}$alkenylOC(O)$R^4$, —$C_2$-$C_{10}$alkynylOC(O)$R^4$, —$C_1$-$C_{10}$alkylOC(O)$OR^4$, —$C_2$-$C_{10}$alkenylOC(O)$OR^4$, —$C_2$-$C_{10}$alkynylOC(O)$OR^4$, —$C_1$-$C_{10}$alkylC(O)N($R^5R^6$), —$C_2$-$C_{10}$alkenylC(O)N($R^5R^6$), —$C_2$-$C_{10}$alkynylC(O)N($R^5R^6$), —$C_1$-$C_{10}$alkylNR$^5$C(O)$R^6$, —$C_2$-$C_{10}$alkenylNR$^5$C(O)$R^6$ and —$C_2$-$C_{10}$alkynylNR$^5$C(O)$R^6$ optionally substituted with one or more amino, hydroxy, $C_1$-$C_4$alkoxy- or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino;

$R^2$ is selected from —$C_{10}$alkyl, —$C_2$-$C_{10}$alkenyl, —$C_2$-$C_{10}$alkynyl, —$C_1$-$C_{10}$alkylC(O)$OR^4$, —$C_2$-$C_{10}$alkenylC(O)$OR^4$, —$C_2$-$C_{10}$alkynylC(O)$OR^4$, —$C_1$-$C_{10}$alkylOC(O)$R^4$, —$C_2$-$C_{10}$alkenylOC(O)$R^4$, —$C_2$-$C_{10}$alkynylOC(O)$R^4$, —$C_1$-$C_{10}$alkylOC(O)$OR^4$, —$C_2$-$C_{10}$alkenylOC(O)$OR^4$, —$C_2$-$C_{10}$alkynylOC(O)$OR^4$, —$C_1$-$C_{10}$alkylC(O)N($R^5R^6$), —$C_2$-$C_{10}$alkenylC(O)N($R^5R^6$), —$C_2$-$C_{10}$alkynylC(O)N($R^5R^6$), —$C_1$-$C_{10}$alkylNR$^5$C(O)$R^6$, —$C_2$-$C_{10}$alkenylNR$^5$C(O)$R^6$ and —$C_2$-$C_{10}$alkynylNR$^5$C(O)$R^6$ optionally substituted with one or more amino, hydroxy, $C_1$-$C_4$alkoxy- or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino;

$R^3$ is H or is selected from —$C_1$-$C_{10}$alkyl, —$C_2$-$C_{10}$alkenyl, —$C_2$-$C_{10}$alkynyl, —$C_1$-$C_{10}$alkylC(O)$OR^4$, —$C_2$-$C_{10}$alkenylC(O)$OR^4$, —$C_2$-$C_{10}$alkynylC(O)$OR^4$, —$C_1$-$C_{10}$alkylOC(O)$R^4$, —$C_2$-$C_{10}$alkenylOC(O)$R^4$, —$C_2$-$C_{10}$alkynylOC(O)$R^4$, —$C_1$-$C_{10}$alkylOC (O)$OR^4$, —$C_2$-$C_{10}$alkenylOC(O)$OR^4$, —$C_2$-$C_{10}$alkynylOC(O)$OR^4$, —$C_1$-$C_{10}$alkylC(O)N($R^5R^6$), —$C_2$-$C_{10}$alkenylC(O)N($R^5R^6$), —$C_2$-$C_{10}$alkynylC(O)N($R^5R^6$), —$C_1$-$C_{10}$alkylNR$^5$C(O)$R^6$, —$C_2$-$C_{10}$alkenylNR$^5$C(O)$R^6$ and —$C_2$-$C_{10}$alkynylNR$^5$C(O)$R^6$ optionally substituted with one or more amino, hydroxy, $C_1$-$C_4$alkoxy- or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino;

$R^4$ is selected from —$C_1$-$C_4$alkyl, —$C_2$-$C_4$alkenyl and —$C_2$-$C_4$alkynyl; and $R^5$ and $R^6$ are independently selected from H, —$C_1$-$C_4$alkyl, —$C_2$-$C_4$alkenyl and —$C_2$-$C_4$alkynyl; or $R^1$ is —$CH_2C(O)OC_1$-$C_4$alkyl and $R^2$ and $R^3$ are each —$CH_2OC(O)C_1$-$C_4$alkyl;

or agriculturally acceptable salts thereof.

These and other aspects of the present invention will become more apparent to the skilled addressee upon reading the following detailed description in connection with the accompanying examples and claims.

BRIEF DESCRIPTION OF THE DRAWINGS

The invention will herein be described by way of example only with reference to the following non-limiting Figures in which.

DETAILED DESCRIPTION OF THE INVENTION

Figure 1:
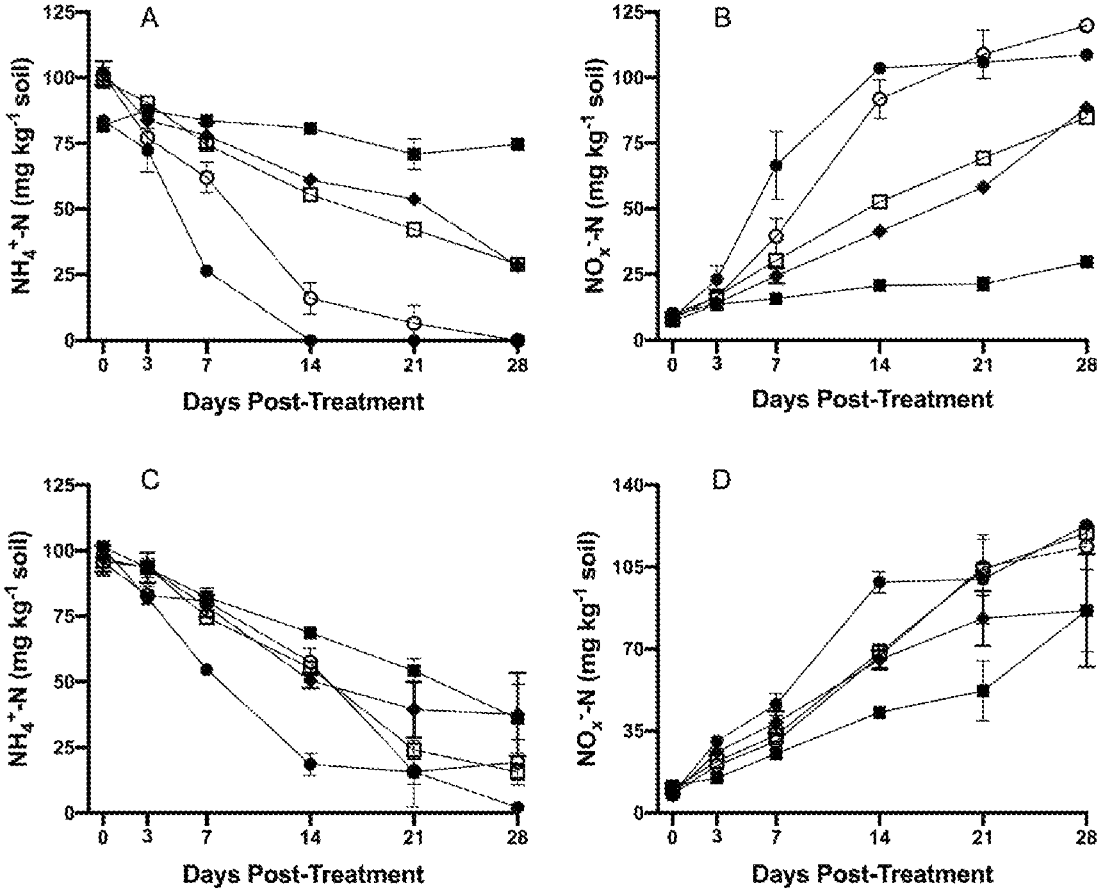
FIG. 1 illustrates the measured $NH_4^+$—N (A, C) and $NO_x^-$—N (B, D) concentrations of Horsham soil incubated at 25° C. (A, B) and 35° C. (C, D) following treatment with: $(NH_4)_2SO_4$ [●], $(NH_4)_2SO_4$+H-DMPP [■], $(NH_4)_2SO_4$+13 [♦], $(NH_4)_2SO_4$+14 [○], $(NH_4)_2SO_4$+16 [□]. Inhibition of nitrification is indicated by a slow decrease of $NH_4^+$—N and slow increase of $NO_x^-$—N.

Mono-, di- and trisubstituted 1,2,3-triazoles were investigated as potential nitrification inhibitors. Substituted 1,2,3-triazoles were seen as a good candidate as they are synthetically readily accessible using copper-catalysed click chemistry approaches and have found application in medicinal and pharmacological fields as a pharmacophore, due to their broad biological activities. Variation of the substitution pattern at the 1, 4 and/or 5 positions allows for optimisation of any inhibitory activity. It is believed that varying the substituents and substitution pattern may enable tailoring of the nitrification inhibitors for certain soils such as acid, neutral and alkaline soils as well as for different climatic conditions.

In one embodiment, the invention provides a method for reducing nitrification in soil comprising treating the soil with a compound of Formula (I):

(I)

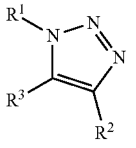

wherein $R^1$ and $R^2$ are independently selected from optionally substituted —$C_1$-$C_{10}$alkyl, —$C_2$-$C_{10}$alkenyl, —$C_2$-$C_{10}$alkynyl, —$C_1$-$C_{10}$alkylC(O)$OR^4$, —$C_2$-$C_{10}$alkenylC(O)$OR^4$, —$C_2$-$C_{10}$alkynylC(O)$OR^4$, —$C_1$-$C_{10}$alkylOC(O)$R^4$, —$C_2$-$C_{10}$alkenylOC(O)$R^4$, —$C_2$-$C_{10}$alkynylOC(O)$R^4$, —$C_1$-$C_{10}$alkylOC(O)$OR^4$, —$C_2$-$C_{10}$alkenylOC(O)$OR^4$, —$C_2$-$C_{10}$alkynylOC(O)$OR^4$, —$C_1$-$C_{10}$alkylC(O)N($R^5R^6$), —$C_2$-$C_{10}$alkenylC(O)N($R^5R^6$), —$C_2$-$C_{10}$alkynylC(O)N($R^5R^6$), —$C_1$-$C_{10}$alkylNR$^5$C(O)$R^6$, —$C_2$-$C_{10}$alkenylNR$^5$C(O)$R^6$ and —$C_2$-$C_{10}$alkynylNR$^5$C(O)$R^6$;

$R^3$ is H or is selected from optionally substituted —$C_1$-$C_{10}$alkyl, —$C_2$-$C_{10}$alkenyl, —$C_2$-$C_{10}$alkynyl, —$C_1$-$C_{10}$alkylC(O)$OR^4$, —$C_2$-$C_{10}$alkenylC(O)$OR^4$, —$C_2$-$C_{10}$alkynylC(O)$OR^4$, —$C_1$-$C_{10}$alkylOC(O)$R^4$, —$C_2$-$C_{10}$alkenylOC(O)$R^4$, —$C_2$-$C_{10}$alkynylOC(O)$R^4$, —$C_1$-$C_{10}$alkylOC(O)$OR^4$, —$C_2$-$C_{10}$alkenylOC(O)$OR^4$, —$C_2$-$C_{10}$alkynylOC(O)$OR^4$, —$C_1$-$C_{10}$alkylC(O)N($R^5R^6$), —$C_2$-$C_{10}$alkenylC(O)N($R^5R^6$), —$C_2$-$C_{10}$alkynylC(O)N($R^5R^6$), —$C_1$-$C_{10}$alkylNR$^5$C(O)$R^6$, —$C_2$-$C_{10}$alkenylNR$^5$C(O)$R^6$ and —$C_2$-$C_{10}$alkynylNR$^5$C(O)$R^6$;

$R^4$ is selected from —$C_1$-$C_4$alkyl, —$C_2$-$C_4$alkenyl and —$C_2$-$C_4$alkynyl; and $R^5$ and $R^6$ are independently selected from H, —$C_1$-$C_4$alkyl, —$C_2$-$C_4$alkenyl and —$C_2$-$C_4$alkynyl;

or agriculturally acceptable salts thereof.

In one embodiment, with reference to Formula (I), $R^1$ and $R^2$ are independently selected from —$C_1$-$C_{10}$alkyl, —$C_2$-$C_{10}$alkenyl, —$C_2$-$C_{10}$alkynyl, —$C_1$-$C_{10}$alkylC(O)O$R^4$, —$C_2$-$C_{10}$alkenylC(O)O$R^4$, —$C_2$-$C_{10}$alkynylC(O)O$R^4$, —$C_1$-$C_{10}$alkylOC(O)$R^4$, —$C_2$-$C_{10}$alkenylOC(O)$R^4$, —$C_2$-$C_{10}$alkynylOC(O)$R^4$, —$C_1$-$C_{10}$alkylOC(O)O$R^4$, —$C_2$-$C_{10}$alkenylOC(O)O$R^4$, —$C_2$-$C_{10}$alkynylOC(O)O$R^4$, —$C_1$-$C_{10}$alkylC(O)N($R^5R^6$), —$C_2$-$C_{10}$alkenylC(O)N($R^5R^6$), —$C_2$-$C_{10}$alkynylC(O)N($R^5R^6$), —$C_1$-$C_{10}$alkylN$R^5$C(O)$R^6$, —$C_2$-$C_{10}$alkenylN$R^5$C(O)$R^6$ and —$C_2$-$C_{10}$alkynylN$R^5$C(O)$R^6$) optionally substituted with one or more amino, hydroxy, $C_1$-$C_4$alkoxy- or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino;

$R^3$ is H or is selected from —$C_1$-$C_{10}$alkyl, —$C_2$-$C_{10}$alkenyl, —$C_2$-$C_{10}$alkynyl, —$C_1$-$C_{10}$alkylC(O)O$R^4$, —$C_2$-$C_{10}$alkenylC(O)O$R^4$, —$C_2$-$C_{10}$alkynylC(O)O$R^4$, —$C_1$-$C_{10}$alkylOC(O)$R^4$, —$C_2$-$C_{10}$alkenylOC(O)$R^4$, —$C_2$-$C_{10}$alkynylOC(O)$R^4$, —$C_1$-$C_{10}$alkylOC(O)O$R^4$, —$C_2$-$C_{10}$alkenylOC(O)O$R^4$, —$C_2$-$C_{10}$alkynylOC(O)O$R^4$, —$C_1$-$C_{10}$alkylC(O)N($R^5R^6$), —$C_2$-$C_{10}$alkenylC(O)N($R^5R^6$), —$C_2$-$C_{10}$alkynylC(O)N($R^5R^6$), —$C_1$-$C_{10}$alkylN$R^5$C(O)$R^6$, —$C_2$-$C_{10}$alkenylN$R^5$C(O)$R^6$ and —$C_2$-$C_{10}$alkynylN$R^5$C(O)$R^6$ optionally substituted with one or more amino, hydroxy, $C_1$-$C_4$alkoxy- or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino;

$R^4$ is selected from —$C_1$-$C_4$alkyl, —$C_2$-$C_4$alkenyl and —$C_2$-$C_4$alkynyl; and $R^5$ and $R^6$ are independently selected from H, —$C_1$-$C_4$alkyl, —$C_2$-$C_4$alkenyl and —$C_2$-$C_4$alkynyl.

In this specification, unless otherwise defined, the term "optionally substituted" is taken to mean that a group may or may not be further substituted with one or more groups selected from hydroxyl, alkyl, alkoxy, alkoxycarbonyl, alkoxycarbonyloxy, alkenyl, alkenyloxy, alkynyl, alkynyloxy, amino, aminoacyl, amido, thio, arylalkyl, arylalkoxy, aryl, aryloxy, acylamino, carboxy, cyano, halogen, nitro, sulfo, phosphono, phosphorylamino, phosphinyl, heteroaryl, heteroaryloxy, heterocyclyl, heterocycloxy, trihalomethyl, pentafluoroethyl, trifluoromethoxy, difluoromethoxy, trifluoromethanethio, trifluoroethenyl, mono- and di-alkylamino, mono- and di-(substituted alkyl)amino, mono- and di-arylamino, mono- and di-heteroarylamino, mono- and di-heterocyclylamino, unsymmetric di-substituted amines having different substituents selected from alkyl, aryl, heteroaryl and heterocyclyl, mono- and di-alkylamido, mono- and di-(substituted alkyl)amido, mono- and di-arylamido, mono- and di-heteroarylamido, mono- and di-heterocyclylamido, unsymmetric di-substituted amides having different substituents selected from alkyl, aryl, heteroaryl and heterocyclyl.

As used herein, the term "alkyl", used either alone or in compound words, denotes straight chain or branched alkyl. Prefixes such as "$C_2$-$C_{10}$" are used to denote the number of carbon atoms within the alkyl group (from 2 to 10 in this case). Examples of straight chain and branched alkyl include methyl, ethyl, n-propyl, isopropyl, n-butyl, sec-butyl, t-butyl, n-pentyl, hexyl, heptyl, 5-methylheptyl, 5-methylhexyl, octyl, nonyl, decyl, undecyl, dodecyl and docosyl ($C_{22}$).

As used herein, the term "alkenyl", used either alone or in compound words, denotes straight chain or branched hydrocarbon residues containing at least one carbon to carbon double bond including ethylenically mono-, di- or polyunsaturated alkyl groups as previously defined. Prefixes such as "$C_2$-$C_{20}$" are used to denote the number of carbon atoms within the alkenyl group (from 2 to 20 in this case). Examples of alkenyl include vinyl, allyl, 1-methylvinyl, butenyl, iso-butenyl, 3-methyl-2-butenyl, 1-pentenyl, 1-hexenyl, 3-hexenyl, 1-heptenyl, 3-heptenyl, 1-octenyl, 1-nonenyl, 2-nonenyl, 3-nonenyl, 1-decenyl, 3-decenyl, 1,3-butadienyl, 1,4-pentadienyl, 1,3-hexadienyl, 1,4-hexadienyl and 5-docosenyl ($C_{22}$).

As used herein, the term "alkynyl", used either alone or in compound words, denotes straight chain or branched hydrocarbon residues containing at least one carbon to carbon triple bond. Prefixes such as "$C_2$-$C_{20}$" are used to denote the number of carbon atoms within the alkenyl group (from 2 to 20 in this case).

The term "amino" as used herein refers to a nitrogen atom substituted with, for example, hydrogen, alkyl, alkenyl, alkynyl, aryl, heteroaryl or combinations thereof.

The term "amido" as used herein refers to an amide group, i.e. a group of the formula —C(O)$NH_2$. The group is bonded to the remainder of the molecule via the carbonyl carbon atom. The nitrogen atom may also be substituted with, for example, alkyl, alkenyl, alkynyl, aryl, heteroaryl or combinations thereof.

The term "aryl" refers to aromatic monocyclic (e.g. phenyl) or polycyclic groups (e.g. tricyclic, bicyclic, e.g., naphthalene, anthryl, phenanthryl). Aryl groups can also be fused or bridged with alicyclic or heterocyclic rings which are not aromatic so as to form a polycycle (e.g. tetralin, methylenedioxyphenyl).

The term "heteroaryl", as used herein, represents a monocyclic or bicyclic ring, typically of up to 7 atoms in each ring, wherein at least one ring is aromatic and contains from 1 to 4 heteroatoms selected from the group consisting of O, N and S. Heteroaryl groups within the scope of this definition include but are not limited to: benzimidazole (otherwise known as benzoimadazole), acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indoiyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

The term "heteroatom" includes atoms of any element other than carbon or hydrogen. Preferred heteroatoms are nitrogen, oxygen, sulfur and phosphorus.

The term "alkoxy" includes substituted and unsubstituted alkyl, alkenyl, and alkynyl groups covalently linked to an oxygen atom. Examples of alkoxy groups include methoxy, ethoxy, isopropyloxy (isopropoxy), propoxy, butoxy, and pentoxy groups and may include cyclic groups such as cyclopentoxy.

In one embodiment, the method as defined above comprises co-treating the soil with a fertiliser.

In another embodiment, the method as defined above is effective for reducing nitrification in soil in an elevated ambient temperature, for example, an ambient temperature of between about 25° C. and about 50° C., such as between about 30° C. and about 45° C.

It will be appreciated that a fertiliser may be formulated to contain a mixture of minerals and nutrients where a source of nitrogen simply provides one of the many minerals and nutrients present in the fertiliser. The fertiliser may be a nitrogen-based fertiliser. The nitrogen-based fertiliser may be an ammonium, ammonium nitrate or urea-based fertiliser, or comprise ammonia, ammonium, nitrate or urea (or may contain all three forms as is the case with urea ammonium nitrate). The nitrogen-based fertiliser may be an organic or inorganic fertiliser. The organic fertiliser may include animal waste. In one embodiment, the fertiliser comprises or consists of an ammonium-based fertiliser. In another embodiment, the fertiliser comprises or consists of a urea-based fertiliser.

In one embodiment, the fertilisers are inorganic fertilisers. These can be ammonium- or urea-containing fertilisers. Examples of ammonium-containing fertilisers of this type are NPK fertilisers, calcium ammonium nitrate, ammonium sulfate nitrate, ammonium sulfate or ammonium phosphate. In a particular embodiment, the ammonium-containing fertilisers are selected from the group consisting of anhydrous ammonia, ammonium sulfate, urea, ammonium nitrate, ammonium phosphate and mixtures thereof.

The fertiliser may be coated or impregnated with the nitrification inhibitor or formulation thereof. The fertiliser may be in the form of granules, crystals or powder incorporating the nitrification inhibitor or formulation thereof. The fertiliser may be a liquid fertiliser comprising the nitrification inhibitor or formulation thereof. It will be appreciated that other forms of fertiliser may be used.

Accordingly, in one embodiment the present invention provides a fertiliser as defined above wherein the urea- or ammonium-based fertiliser is in the form of a granule and the compound of Formula (I) is coated on the granule.

In a further embodiment, the method as defined above comprises co-treating the soil with a urease inhibitor.

Currently, there is only one commercially available urease inhibitor, N-(n-butyl) thiophosphoric triamide (NBPT, marketed as Agrotain). Unfortunately, the lifetime of this inhibitor in soils is limited. The major degradation pathway in acidic and slightly alkaline soils is chemical hydrolysis, whereas microbial degradation becomes dominant in more alkaline soils.

Most soil conditions would benefit from fertilisers that contain both urease and nitrification inhibitors. Furthermore, recent research suggests that, while nitrification inhibitors are effective in reducing $N_2O$ emission from various agricultural systems, they may increase $NH_3$ emission under certain conditions. These problems highlight the importance of using both urease and nitrification inhibitors in mitigating nitrogen loss. At present, there are limited commercial products which combine both urease and nitrification inhibitors, since production is hampered by the challenge of combining acid-sensitive NBPT with the acidic DMPP.

In one embodiment, there is provided a fertiliser as defined above wherein the urea- or ammonium-based fertiliser is in the form of a granule and the compound of Formula (I) and a urease inhibitor are coated on the granule.

In one embodiment, the invention provides a compound of Formula (II):

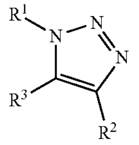

(II)

wherein $R^1$ and $R^2$ are independently selected from optionally substituted —$C_1$-$C_{10}$alkyl, —$C_2$-$C_{10}$alkenyl, —$C_2$-$C_{10}$alkynyl, —$C_1$-$C_{10}$alkylC(O)O$R^4$, —$C_2$-$C_{10}$alkenylC(O)O$R^4$, —$C_2$-$C_{10}$alkynylC(O)O$R^4$, —$C_1$-$C_{10}$alkylOC(O)$R^4$, —$C_2$-$C_{10}$alkenylOC(O)$R^4$, —$C_2$-$C_{10}$alkynylOC(O)$R^4$, —$C_1$-$C_{10}$alkylOC(O)O$R^4$, —$C_2$-$C_{10}$alkenylOC(O)O$R^4$, —$C_2$-$C_{10}$alkynylOC(O)O$R^4$, —$C_1$-$C_{10}$alkylC(O)N($R^5R^6$), —$C_2$-$C_{10}$alkenylC(O)N($R^5R^6$), —$C_2$-$C_{10}$alkynylC(O)N($R^5R^6$), —$C_1$-$C_{10}$alkylN$R^5$C(O)$R^6$, —$C_2$-$C_{10}$alkenylN$R^5$C(O)$R^6$ and —$C_2$-$C_{10}$alkynylN$R^5$C(O)$R^6$;

$R^3$ is H or is selected from optionally substituted —$C_1$-$C_{10}$alkyl, —$C_2$-$C_{10}$alkenyl, —$C_2$-$C_{10}$alkynyl, —$C_1$-$C_{10}$alkylC(O)O$R^4$, —$C_2$-$C_{10}$alkenylC(O)O$R^4$, —$C_2$-$C_{10}$alkynylC(O)O$R^4$, —$C_1$-$C_{10}$alkylOC(O)$R^4$, —$C_2$-$C_{10}$alkenylOC(O)$R^4$, —$C_2$-$C_{10}$alkynylOC(O)$R^4$, —$C_1$-$C_{10}$alkylOC(O)O$R^4$, —$C_2$-$C_{10}$alkenylOC(O)O$R^4$, —$C_2$-$C_{10}$alkynylOC(O)O$R^4$, —$C_1$-$C_{10}$alkylC(O)N($R^5R^6$), —$C_2$-$C_{10}$alkenylC(O)N($R^5R^6$), —$C_2$-$C_{10}$alkynylC(O)N($R^5R^6$), —$C_1$-$C_{10}$alkylN$R^5$C(O)$R^6$, —$C_2$-$C_{10}$alkenylN$R^5$C(O)$R^6$ and —$C_2$-$C_{10}$alkynylN$R^5$C(O)$R^6$;

$R^4$ is selected from —$C_1$-$C_4$alkyl, —$C_2$-$C_4$alkenyl and —$C_2$-$C_4$alkynyl; and $R^5$ and $R^6$ are independently selected from H, —$C_1$-$C_4$alkyl, —$C_2$-$C_4$alkenyl and —$C_2$-$C_4$alkynyl;

provided that the compound is not:

1-butyl-4-pentyl-1H-1,2,3-triazole;

1,4-butyl-1H-1,2,3-triazole;

4-butyl-1H-1,2,3-triazole-1-acetic acid ethyl ester;

1-butyl-4-(α,α-dimethyl methanol)-1H-1,2,3-triazole;

4-butyl-1H-1,2,3-triazole-1-propanamine;

ethyl 4,5-bis(hydroxymethyl)-1H-1,2,3-triazole-1-acetate; or 1,4-dipropyl-1H-1,2,3-triazole;

or agriculturally acceptable salts thereof.

In some preferred embodiments of the invention, and with reference to the general Formula (II), one or more of the following preferred embodiments apply:

(a) $R^1$ is $C_1$-$C_{10}$alkyl substituted with one or more hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(b) $R^1$ is selected from —$C_2$-$C_{10}$alkenyl, —$C_2$-$C_{10}$alkynyl, —$C_2$-$C_{10}$alkylC(O)O$C_1$-$C_4$alkyl, —$C_1$-$C_{10}$alkylC(O)O$C_2$-$C_4$alkenyl, —$C_1$-$C_{10}$alkylC(O)O$C_2$-$C_4$alkynyl, —$C_2$-$C_{10}$alkenylC(O)O$R^4$, —$C_2$-$C_{10}$alkynylC(O)O$R^4$, —$C_1$-$C_{10}$alkylOC(O)$R^4$, —$C_2$-$C_{10}$alkenylOC(O)$R^4$, —$C_2$-$C_{10}$alkynylOC(O)$R^4$, —$C_1$-$C_{10}$alkylOC(O)O$R^4$, —$C_2$-$C_{10}$alkenylOC(O)O$R^4$, —$C_2$-$C_{10}$alkynylOC(O)O$R^4$, —$C_1$-$C_{10}$alkylC(O)

$N(R^5R^6)$, —$C_2$-$C_{10}$alkenyl$C(O)N(R^5R^6)$, —$C_2$-$C_{10}$alkynyl$C(O)N(R^5R^6)$, —$C_1$-$C_{10}$alkyl$NR^5C(O)R^6$, —$C_2$-$C_{10}$alkenyl$NR^5C(O)R^6$ and —$C_2$-$C_{10}$alkynyl$NR^5C(O)R^6$ optionally substituted with one or more amino, hydroxy, $C_1$-$C_4$alkoxy- or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(c) $R^1$ is $C_1$-$C_{10}$alkyl substituted with a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(d) $R^1$ is $C_1$-$C_{10}$alkyl substituted with isoindoline-1,3-dione.

(e) $R^1$ is $C_1$-$C_{10}$alkyl substituted with one or more hydroxyl.

(f) $R^1$ is $C_1$-$C_{10}$alky substituted with one or more $C_1$-$C_4$alkoxy-.

(g) $R^1$ is $C_2$-$C_{10}$alkenyl optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(h) $R^1$ is $C_2$-$C_{10}$alkynyl optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(i) $R^1$ is —$C_2$-$C_{10}$alkyl$C(O)OC_1$-$C_4$alkyl optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(j) $R^1$ is —$C_1$-$C_{10}$alkyl$C(O)OC_2$-$C_4$alkenyl optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(k) $R^1$ is —$C_1$-$C_{10}$alkyl$C(O)OC_2$-$C_4$alkynyl optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(l) $R^1$ is —$C_2$-$C_{10}$alkenyl$C(O)OR^4$ optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(m) $R^1$ is —$C_2$-$C_{10}$alkynyl$C(O)OR^4$ optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(n) $R^1$ is —$C_1$-$C_{10}$alkyl$OC(O)R^4$ optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(o) $R^1$ is —$C_2$-$C_{10}$alkenyl$OC(O)R^4$ optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(p) $R^1$ is —$C_2$-$C_{10}$alkynyl$OC(O)R^4$ optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(q) $R^1$ is —$C_1$-$C_{10}$alkyl$OC(O)OR^4$ optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(r) $R^1$ is —$C_2$-$C_{10}$alkenyl$OC(O)OR^4$ optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(s) $R^1$ is —$C_2$-$C_{10}$alkynyl$OC(O)OR^4$ optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(t) $R^1$ is —$C_1$-$C_{10}$alkyl$C(O)N(R^5R^6)$ optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(u) $R^1$ is —$C_2$-$C_{10}$alkenyl$C(O)N(R^5R^6)$ optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(v) $R^1$ is —$C_2$-$C_{10}$alkynyl$C(O)N(R^5R^6)$ optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(w) $R^1$ is —$C_1$-$C_{10}$alkylNR$^5$C(O)R$^6$ optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(x) $R^1$ is —$C_2$-$C_{10}$alkenylNR$^5$C(O)R$^6$ optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(y) $R^1$ is —$C_2$-$C_{10}$alkynylNR$^5$C(O)R$^6$ optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(z) $R^1$ is —$C_3$-$C_{10}$alkyl(O)O$C_1$-$C_4$alkyl.

(aa) $R^2$ is selected from —$C_1$-$C_{10}$alkyl, —$C_2$-$C_{10}$alkenyl, —$C_2$-$C_{10}$alkynyl, —$C_1$-$C_{10}$alkylC(O)OR$^4$, —$C_2$-$C_{10}$alkenylC(O)OR$^4$, —$C_2$-$C_{10}$alkynylC(O)OR$^4$, —$C_1$-$C_{10}$alkylOC(O)R$^4$, —$C_2$-$C_{10}$alkenylOC(O)R$^4$, —$C_2$-$C_{10}$alkynylOC(O)R$^4$, —$C_1$-$C_{10}$alkylOC(O)OR$^4$, —$C_2$-$C_{10}$alkenylOC(O)OR$^4$, —$C_2$-$C_{10}$alkynylOC(O)OR$^4$, —$C_1$-$C_{10}$alkylC(O)N(R$^5$R$^6$), —$C_2$-$C_{10}$alkenylC(O)N(R$^5$R$^6$), —$C_2$-$C_{10}$alkynylC(O)N(R$^5$R$^6$), —$C_1$-$C_{10}$alkylNR$^5$C(O)R$^6$, —$C_2$-$C_{10}$alkenylNR$^5$C(O)R$^6$ and —$C_2$-$C_{10}$alkynylNR$^5$C(O)R$^6$ optionally substituted with one or more amino, hydroxy, $C_1$-$C_4$alkoxy- or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(ab) $R^2$ is $C_1$-$C_{10}$alkyl, optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(ac) $R^2$ is unsubstituted $C_1$-$C_{10}$alkyl.

(ad) $R^2$ is unsubstituted —$C_1$-$C_{10}$alkylOC(O)R$^4$.

(ae) $R^2$ is $C_1$-$C_{10}$alkyl optionally substituted with hydroxy.

(af) $R^2$ is $C_2$-$C_{10}$alkenyl optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(ag) $R^2$ is $C_2$-$C_{10}$alkynyl optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(ah) $R^2$ is —$C_1$-$C_{10}$alkylC(O)OR$^4$ optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(ai) $R^2$ is —$C_2$-$C_{10}$alkenylC(O)OR$^4$ optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(aj) $R^2$ is —$C_2$-$C_{10}$alkynylC(O)OR$^4$ optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(ak) $R^2$ is —$C_1$-$C_{10}$alkylOC(O)R$^4$ optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(al) $R^2$ is —$C_2$-$C_{10}$alkenylOC(O)R$^4$ optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(am) $R^2$ is —$C_2$-$C_{10}$alkynylOC(O)R$^4$ optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(an) $R^2$ is —$C_1$-$C_{10}$alkylOC(O)OR$^4$ optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(ao) $R^2$ is —$C_2$-$C_{10}$alkenylOC(O)OR$^4$ optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(ap) $R^2$ is —$C_2$-$C_{10}$alkynylOC(O)OR$^4$ optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(aq) $R^2$ is —$C_1$-$C_{10}$alkylC(O)N(R$^5$R$^6$) optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(ar) $R^2$ is —$C_2$-$C_{10}$alkenylC(O)N($R^5R^6$) optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(as) $R^2$ is —$C_2$-$C_{10}$alkynylC(O)N($R^5R^6$) optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(at) $R^2$ is —$C_1$-$C_{10}$alkylN$R^5$C(O)$R^6$ optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(au) $R^2$ is —$C_2$-$C_{10}$alkenylN$R^5$C(O)$R^6$ optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(av) $R^2$ is —$C_2$-$C_{10}$alkynylN$R^5$C(O)$R^6$ optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(aw) $R^3$ is H or is selected from —$C_1$-$C_{10}$alkyl, —$C_2$-$C_{10}$alkenyl, —$C_2$-$C_{10}$alkynyl, —$C_1$-$C_{10}$alkylC(O)O$R^4$, —$C_2$-$C_{10}$alkenylC(O)O$R^4$, —$C_2$-$C_{10}$alkynylC(O)O$R^4$, —$C_1$-$C_{10}$alkylOC(O)$R^4$, —$C_2$-$C_{10}$alkenylOC(O)$R^4$, —$C_2$-$C_{10}$alkynylOC(O)$R^4$, —$C_1$-$C_{10}$alkylOC(O)O$R^4$, —$C_2$-$C_{10}$alkenylOC(O)O$R^4$, —$C_2$-$C_{10}$alkynylOC(O)O$R^4$, —$C_1$-$C_{10}$alkylC(O)N($R^5R^6$), —$C_2$-$C_{10}$alkenylC(O)N($R^5R^6$), —$C_2$-$C_{10}$alkynylC(O)N($R^5R^6$), —$C_1$-$C_{10}$alkylN$R^5$C(O)$R^6$, —$C_2$-$C_{10}$alkenylN$R^5$C(O)$R^6$ and —$C_2$-$C_{10}$alkynylN$R^5$C(O)$R^6$ optionally substituted with one or more amino, hydroxy, $C_1$-$C_4$alkoxy- or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(ax) $R^3$ is $C_2$-$C_{10}$alkyl optionally substituted with one or more amino, hydroxy, $C_1$-$C_4$alkoxy- or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(ay) $R^3$ is —$C_1$-$C_{10}$alkyl substituted with hydroxyl.

(az) $R^3$ is —$C_2$-$C_{10}$alkenyl optionally substituted with one or more amino, hydroxy, $C_1$-$C_4$alkoxy- or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(ba) $R^3$ is —$C_2$-$C_{10}$alkynyl optionally substituted with one or more amino, hydroxy, $C_1$-$C_4$alkoxy- or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(bb) $R^3$ is —$C_1$-$C_{10}$alkylC(O)O$R^4$ optionally substituted with one or more amino, hydroxy, $C_1$-$C_4$alkoxy- or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(bc) $R^3$ is —$C_2$-$C_{10}$alkenylC(O)O$R^4$ optionally substituted with one or more amino, hydroxy, $C_1$-$C_4$alkoxy- or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(bd) $R^3$ is —$C_2$-$C_{10}$alkynylC(O)O$R^4$ optionally substituted with one or more amino, hydroxy, $C_1$-$C_4$alkoxy- or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(be) $R^3$ is —$C_1$-$C_{10}$alkylOC(O)$R^4$ optionally substituted with one or more amino, hydroxy, $C_1$-$C_4$alkoxy- or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(bf) $R^3$ is —$C_2$-$C_{10}$alkenylOC(O)$R^4$ optionally substituted with one or more amino, hydroxy, $C_1$-$C_4$alkoxy- or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(bg) $R^3$ is —$C_2$-$C_{10}$alkynylOC(O)$R^4$ optionally substituted with one or more amino, hydroxy, $C_1$-$C_4$alkoxy- or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(bh) $R^3$ is —$C_1$-$C_{10}$alkylOC(O)O$R^4$ optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(bi) $R^3$ is —$C_2$-$C_{10}$alkenylOC(O)O$R^4$ optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(bj) $R^3$ is —$C_2$-$C_{10}$alkynylOC(O)O$R^4$ optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(bk) $R^3$ is $C_1$-$C_{10}$alkylC(O)N($R^5R^6$) optionally substituted with one or more amino, hydroxy, $C_1$-$C_4$alkoxy- or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(bl) $R^3$ is —$C_2$-$C_{10}$alkenylC(O)N($R^5R^6$) optionally substituted with one or more amino, hydroxy, $C_1$-$C_4$alkoxy- or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(bm) $R^3$ is —$C_1$-$C_{10}$alkylNR$^5$C(O)R$^6$ optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(bn) $R^3$ is —$C_2$-$C_{10}$alkenylNR$^5$C(O)R$^6$ optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(bo) $R^3$ is —$C_2$-$C_{10}$alkynylNR$^5$C(O)R$^6$ optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino.

(bp) $R^3$ is unsubstituted —$C_1$-$C_{10}$alkylOC(O)R$^4$.

(bq) $R^4$ is selected from $C_1$-$C_4$alkyl, $C_2$-$C_4$alkenyl and $C_2$-$C_4$alkynyl (br) $R^4$ is $C_1$-$C_4$alkyl.

(bs) $R^4$ is ethyl.

(bt) $R^5$ and $R^6$ are independently selected from H, $C_1$-$C_4$alkyl, $C_2$-$C_4$alkenyl and $C_2$-$C_4$alkynyl.

(bu) one of $R^5$ and $R^6$ is H and the other is $C_1$-$C_4$alkyl, $C_2$-$C_4$alkenyl or $C_2$-$C_4$alkynyl.

(bv) $R^1$ is —$CH_2C(O)OC_1$-$C_4$alkyl and $R^2$ and $R^3$ are each —$CH_2OC(O)C_1$-$C_4$alkyl.

Accordingly, in one aspect the present invention provides a compound of the Formula (II) represented by the Formula (IIa):

(IIa)

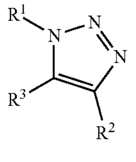

wherein $R^1$ is —$C_1$-$C_{10}$alkyl substituted with one or more hydroxy, —$C_1$-$C_4$alkoxy- or 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino; or $R^1$ is selected from —$C_2$-$C_{10}$alkenyl, —$C_2$-$C_{10}$alkynyl, —$C_2$-$C_{10}$alkylC(O)OC$_1$-$C_4$alkyl, —$C_1$-$C_{10}$alkylC(O)OC$_2$-$C_4$alkenyl, —$C_1$-$C_{10}$alkylC(O)OC$_2$-$C_4$alkynyl, —$C_2$-$C_{10}$alkenylC(O)OR$^4$, —$C_2$-$C_{10}$alkynylC(O)OR$^4$, —$C_1$-$C_{10}$alkylOC(O)R$^4$, —$C_2$-$C_{10}$alkenylOC(O)R$^4$, —$C_2$-$C_{10}$alkynylOC(O)R$^4$, —$C_1$-$C_{10}$alkylOC(O)OR$^4$, —$C_2$-$C_{10}$alkenylOC(O)OR$^4$, —$C_2$-$C_{10}$alkynylOC(O)OR$^4$, —$C_1$-$C_{10}$alkylC(O)N($R^5R^6$), —$C_2$-$C_{10}$alkenylC(O)N($R^5R^6$), —$C_2$-$C_{10}$alkynylC(O)N($R^5R^6$), —$C_1$-$C_{10}$alkylNR$^5$C(O)R$^6$, —$C_2$-$C_{10}$alkenylNR$^5$C(O)R$^6$ and —$C_2$-$C_{10}$alkynylNR$^5$C(O)R$^6$ optionally substituted with one or more amino, hydroxy, $C_1$-$C_4$alkoxy- or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino;

$R^2$ is selected from —$C_{10}$alkyl, —$C_2$-$C_{10}$alkenyl, —$C_2$-$C_{10}$alkynyl, —$C_1$-$C_{10}$alkylC(O)OR$^4$, —$C_2$-$C_{10}$alkenylC(O)OR$^4$, —$C_2$-$C_{10}$alkynylC(O)OR$^4$, —$C_1$-$C_{10}$alkylOC(O)R$^4$, —$C_2$-$C_{10}$alkenylOC(O)R$^4$, —$C_2$-$C_{10}$alkynylOC(O)R$^4$, —$C_1$-$C_{10}$alkylOC(O)OR$^4$, —$C_2$-$C_{10}$alkenylOC(O)OR$^4$, —$C_2$-$C_{10}$alkynylOC(O)OR$^4$, —$C_1$-$C_{10}$alkylC(O)N($R^5R^6$), —$C_2$-$C_{10}$alkenylC(O)N($R^5R^6$), —$C_2$-$C_{10}$alkynylC(O)N($R^5R^6$), —$C_1$-$C_{10}$alkylNR$^5$C(O)R$^6$, —$C_2$-$C_{10}$alkenylNR$^5$C(O)R$^6$ and —$C_2$-$C_{10}$alkynylNR$^5$C(O)R$^6$ optionally substituted with one or more amino, hydroxy, $C_1$-$C_4$alkoxy- or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino;

$R^3$ is H or is selected from —$C_1$-$C_{10}$alkyl, —$C_2$-$C_{10}$alkenyl, —$C_2$-$C_{10}$alkynyl, —$C_1$-$C_{10}$alkylC(O)OR$^4$, —$C_2$-$C_{10}$alkenylC(O)OR$^4$, —$C_2$-$C_{10}$alkynylC(O)OR$^4$, —$C_1$-$C_{10}$alkylOC(O)R$^4$, —$C_2$-$C_{10}$alkenylOC(O)R$^4$, —$C_2$-$C_{10}$alkynylOC(O)R$^4$, —$C_1$-$C_{10}$alkylOC(O)OR$^4$, —$C_2$-$C_{10}$alkenylOC(O)OR$^4$, —$C_2$-$C_{10}$alkynylOC(O)OR$^4$, —$C_1$-$C_{10}$alkylC(O)N($R^5R^6$), —$C_2$-$C_{10}$alkenylC(O)N($R^5R^6$), —$C_2$-$C_{10}$alkynylC(O)N($R^5R^6$), —$C_1$-$C_{10}$alkylNR$^5$C(O)R$^6$, —$C_2$-$C_{10}$alkenylNR$^5$C(O)R$^6$ and —$C_2$-$C_{10}$alkynylNR$^5$C(O)R$^6$ optionally substituted with one or more amino, hydroxy, $C_1$-$C_4$alkoxy- or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino;

$R^4$ is selected from —$C_1$-$C_4$alkyl, —$C_2$-$C_4$alkenyl and —$C_2$-$C_4$alkynyl; and $R^5$ and $R^6$ are independently selected from H, —$C_1$-$C_4$alkyl, —$C_2$-$C_4$alkenyl and —$C_2$-$C_4$alkynyl; or $R^1$ is —$CH_2C(O)OC_1$-$C_4$alkyl and $R^2$ and $R^3$ are each —$CH_2OC(O)C_1$-$C_4$alkyl;

or agriculturally acceptable salts thereof.

In a further embodiment, with reference to Formula (IIa), $R^1$ is selected from $C_2$-$C_{10}$alkenyl, $C_2$-$C_{10}$alkynyl, —$C_2$-$C_{10}$alkylC(O)OC$_1$-$C_4$alkyl, —$C_1$-$C_{10}$alkylC(O)OC$_2$-$C_4$alkenyl, —$C_1$-$C_{10}$alkylC(O)OC$_2$-$C_4$alkynyl, —$C_2$-$C_{10}$alkenylC(O)OR$^4$, —$C_2$-$C_{10}$alkynylC(O)OR$^4$, —$C_1$-$C_{10}$alkylC(O)N($R^5R^6$), —$C_2$-$C_{10}$alkenylC(O)N($R^5R^6$) and —$C_2$-$C_{10}$alkynylC(O)N($R^5R^6$) optionally substituted with one or more amino, hydroxy, $C_1$-$C_4$alkoxy- or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino;

$R^2$ is selected from —$C_{10}$alkyl, —$C_2$-$C_{10}$alkenyl, —$C_2$-$C_{10}$alkynyl, —$C_1$-$C_{10}$alkylOC(O)$R^4$, —$C_2$-$C_{10}$alkenylOC(O)$R^4$ and —$C_2$-$C_{10}$alkynylOC(O)$R^4$ optionally substituted with one or more amino, hydroxy, $C_1$-$C_4$alkoxy-, or a 3-10-membered monocyclic or fused bicyclic heteroaryl comprising one or more heteroatoms selected from N, O and S, wherein said heteroaryl is optionally substituted with one or more $C_1$-$C_{10}$alkyl, oxo, hydroxy, $C_1$-$C_4$alkoxy- or amino;

$R^3$ is H or is selected from —$C_1$-$C_{10}$alkyl, —$C_2$-$C_{10}$alkenyl, —$C_2$-$C_{10}$alkynyl, —$C_1$-$C_{10}$alkylOC(O)$R^4$, —$C_2$-$C_{10}$alkenylOC(O)$R^4$ and —$C_2$-$C_{10}$alkynylOC(O)$R^4$ optionally substituted with one or more amino, hydroxyl, or $C_1$-$C_4$alkoxy;

$R^4$ is selected from $C_1$-$C_4$alkyl, $C_2$-$C_4$alkenyl and $C_2$-$C_4$alkynyl; and $R^5$ and $R^6$ are independently selected from H, $C_1$-$C_4$alkyl, $C_2$-$C_4$alkenyl and $C_2$-$C_4$alkynyl In another embodiment, the compound of Formula (IIa), or agriculturally acceptable salt thereof, is selected from:

4-butyl-1H-1,2,3-triazole-1-butanoic acid ethyl ester (5);
2-[3-[4,5-di(hydroxymethyl)-1H-1,2,3-triazole]propyl]-isoindoline-1,3-dione (7);
2-[3-[4,5-(methyl ethanoate)-1H-1,2,3-triazole]propyl]-isoindoline-1,3-dione (8);
ethyl 4,5-bis(hydroxymethyl)-1H-1,2,3-triazole-1-butyrate (9);
ethyl 4,5-bis(methyl ethanoate)-1H-1,2,3-triazole-1-butyrate (10);
ethyl 4,5-bis(methyl ethanoate)-1H-1,2,3-triazole-1-acetate (11);
1-butyl-4-propyl-1H-1,2,3-triazole (13);
1-(2-methoxyethyl)-4-butyl-1H-1,2,3-triazole (14);
4-propyl-1H-1,2,3-triazole-1-ethanol (15);
1-(3-butyn-1-yl)-4-propyl-1H-1,2,3-triazole (17);
1-(2-propen-1-yl)-4-propyl-1H-1,2,3-triazole (18);
ethyl 2-(4-propyl-1H-1,2,3-triazol-1-yl)-acetate (19);
prop-2-en-1-yl 2-(4-propyl-1H-1,2,3-triazol-1-yl)-acetate (20);
prop-2-en-1-yl 2-(4-propyl-1H-1,2,3-triazol-1-yl)-acetamide (21);
prop-2-yn-1-yl 2-(4-propyl-1H-1,2,3-triazol-1-yl)-acetate (22); and
prop-2-yn-1-yl 2-(4-propyl-1H-1,2,3-triazol-1-yl)-acetamide (23).

It will be understood that the compounds of the invention may exist in a plurality of equivalent tautomeric forms. For the sake of clarity, the compounds have been depicted as single tautomers, despite all such tautomeric forms being considered within the scope of the invention.

The structures of some of the compounds of the invention may include asymmetric carbon atoms. It is to be understood accordingly that the isomers arising from such asymmetry (e.g., all enantiomers, stereoisomers, rotamers, tautomers, diastereomers, or racemates) are included within the scope of this invention. The present invention includes within its scope all of these stereoisomeric forms either isolated (in, for example, enantiomeric isolation), or in combination (including racemic mixtures and diastereomic mixtures).

The skilled person will appreciate that there are a range of techniques available to produce achiral compounds of the invention in racemic, enantioenriched or enantiopure forms. For example, enantioenriched or enantiopure forms of the compounds may be produced through stereoselective synthesis and/or through the use of chromatographic or selective recrystallisation techniques.

The compounds of the invention may be in crystalline form, may be oils or may be solvates (e.g. hydrates), and it is intended that all forms are within the scope of the present invention. The term "solvate" is a complex of variable stoichiometry formed by a solute (in this invention, a compound of the invention) and a solvent. Such solvents should preferably not interfere with the biological activity of the solute. Solvents may be, by way of example, water, acetone, ethanol or acetic acid. Methods of solvation are generally known within the art.

The compounds of the invention that have at least one basic centre can form acid addition salts. Acid addition salts may be prepared from inorganic and organic acids. Examples of inorganic acids include hydrochloric acid, hydrobromic acid, sulfuric acid, nitric acid, phosphoric acid and the like. Examples of organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

The compounds of the invention which have at least one acidic group can form base addition salts. Base addition salts may be prepared from inorganic and organic bases. Corresponding counterions derived from inorganic bases include the sodium, potassium, lithium, ammonium, calcium and magnesium salts. Organic bases include primary, secondary and tertiary amines, substituted amines including naturally-occurring substituted amines, and cyclic amines, including isopropylamine, trimethyl amine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, and N-ethylpiperidine.

In a further aspect there is provided a composition for reducing nitrification in soil comprising a compound of Formula (I) as defined herein and at least one agriculturally acceptable adjuvant or diluent.

The compounds according to the invention can be used as nitrification inhibitors in unmodified form but are generally formulated into compositions in various ways using formulation adjuvants, such as carriers, solvents and surface-active substances. The formulations can be in various physical forms, for example, in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspo-emulsions, capsule suspensions, emulsifiable granules, soluble liquids, water-soluble concentrates (with water or a water-miscible organic solvent as carrier), impregnated polymer films or in other known forms. Such formulations can either be used directly or diluted prior to use. The dilutions can be made, for example, with a diluent selected from but not limited to water, liquid fertilisers, micronutrients, biological organisms, oil or solvents.

The formulations can be prepared by mixing the nitrification inhibitor of the invention with the formulation adjuvants in order to obtain compositions in the form of finely divided solids, granules, solutions, dispersions or emulsions. The nitrification inhibitors can also be formulated with other adjuvants, such as finely divided solids, mineral oils, oils of vegetable or animal origin, modified oils of vegetable or animal origin, organic solvents, water, surface-active substances or combinations thereof.

The nitrification inhibitors can also be contained in very fine microcapsules. Microcapsules contain the active ingredients in a porous carrier to enable release of the nitrification inhibitors into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitriles, polyacrylates, polyesters, polyamides, polyureas, polyurethanes or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

Formulation adjuvants that are suitable for the preparation of the compositions according to the invention are known in the art. As liquid carriers there may be used: water, toluene, xylene, petroleum ether, vegetable oils, acetone, methyl ethyl ketone, sulfolane (tetramethylene sulfone), cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxy-propanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophillite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric, and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood N.J. (1981).

Further adjuvants that can be used in nitrification inhibitor formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers.

The compositions according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. As an example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example, the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively).

The compositions according to the invention generally comprise from 0.1 to 99% by weight, especially from 0.1 to 95% by weight, of compounds of the present invention and from 1 to 99.9% by weight of a formulation adjuvant which may include from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the type of fertiliser used, the prevailing climatic conditions, and other factors governed by the method of application, the time of application and the target crop. As a general guideline compounds may be applied at a rate of from 1 to 2000 L/ha, especially from 10 to 1000 L/ha.

The composition may further comprise a urease inhibitor.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The invention will now be described with reference to the following non-limiting examples:

1. Synthesis of Nitrification Inhibitors

1.1 General

Reaction progress was monitored by thin-layer chromatography (TLC) using silica gel 60 aluminium-backed plates coated with fluorescent indicator F254 (Merck). Plates were visualised using UV irradiation (254 nm) alone or in conjunction with ninhydrin-, potassium permanganate- or iodine-based stains. Purification by silica gel chromatography was performed using Davisil Chromatographic Silica Media LC60A 40-63 micron, with solvent systems as specified. All $^{1}H$ and $^{13}C$ NMR spectra were recorded on a 400 MHz Varian INOVA spectrometer (at 400 or 101 MHz, respectively) downfield from residual solvents peaks using solvent resonances as the internal standard ($^{1}H$ NMR: $CDCl_3$ at 7.26 ppm, DMSO-$d_6$ at 2.50 ppm; $^{13}C$ NMR: $CDCl_3$ at 77.0 ppm, DMSO-$d_6$ at 39.5 ppm). Chemical shifts are reported in parts per million (ppm, δ), with the splitting patterns indicated as follows: s, singlet; d, doublet; t, triplet; q, quartet; p, pentet; m, multiplet; dd, doublet of doublets. The coupling constants, J, are reported in Hertz (Hz). Electrospray ionization high resolution mass spectrometry (HRMS) was performed on a Thermo Scientific Exactive Plus Orbitrap mass spectrometer (Thermo, Bremen, German) operated in positive mode.

1.2 General Procedure A: Copper(I)-Catalysed Azide-Alkyne Cycloaddition (CuAAC) to Synthesise 1,4-Disubstituted Triazoles Scheme 1: Reaction scheme for General Procedure A.

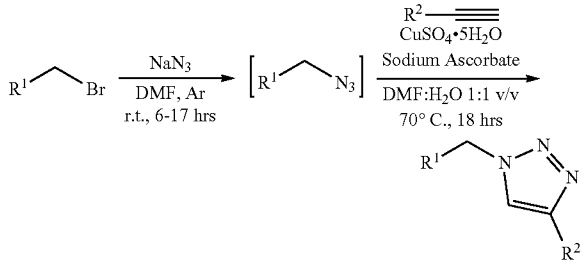

Sodium azide (1.2 or 1.5 equiv.) was suspended in DMF (0.85 M) in a flask under argon atmosphere, and to this the appropriate alkyl bromide (1 eq.) was added. The solution was stirred at room temperature for 6-17 hours. The reaction was quenched by the addition of $H_2O$ (DMF/$H_2O$, 1:1 v/v), before the successive additions of $CuSO_4 \cdot 5H_2O$ (0.06 equiv.), sodium ascorbate (0.3 equiv.) and the appropriate alkyne (1.2 or 1.5 equiv.). The reaction was heated at 70° C. overnight with vigorous stirring. The reaction was cooled to room temperature before dilution with $H_2O$ (at least 3×DMF volume) and extraction with ethyl acetate. The extracts were combined, washed with 5% aq. LiCl solution and concentrated before purification by silica chromatography.

1.3 General Procedure B: Thermal Huisgen 1,3-Dipolar Cycloaddition to Synthesise 1,4,5-Trisubstituted Triazoles Scheme 2: Reaction scheme for General Procedure B.

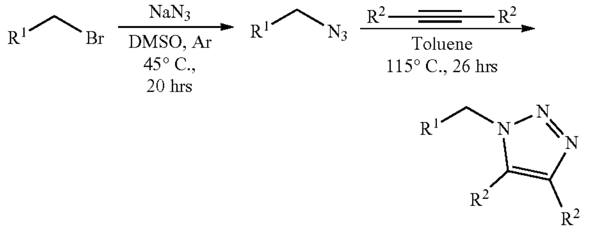

Sodium azide (1.5 equiv.) and appropriate alkyl bromide (1 equiv.) were charged into a flask flushed with argon. They were suspended in DMSO (1.28 M) and warmed to 45° C. with vigorous stirring. The reaction was cooled to room temperature after 20 hours and quenched with $H_2O$ (DMF/$H_2O$, 4:5 v/v), before extraction with ether. The ethereal extracts were concentrated under $N_2$ flow to an oil, which was used directly in the subsequent step. *CAUTION: Organic azides may be explosive, do not evaporate to dryness. Smaller azides were handled using solvent substitution, where toluene was added before ether was evaporated under $N_2$ flow.

The crude azide was suspended in toluene (0.21 M) before addition of the appropriate internal alkyne (1.1 equiv.). The reaction was then heated at 115° C. with vigorous stirring. Once completed by TLC (24 to 48 hrs), the reaction was cooled. Toluene was removed in vacuo to leave crude triazole as a waxy brown solid. Purification of the crude product was achieved through recrystallisation or column chromatography.

1.4 Synthesis of 1-butyl-4-pentyl-1H-1,2,3-triazole (1)

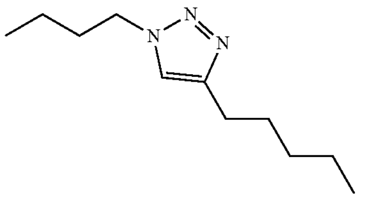

Synthesised from General Procedure A; 1 (2.14 g, 11.0 mmol, 64%) was obtained starting from sodium azide (25.6 mmol), 1-bromobutane (17.1 mmol), $CuSO_4 \cdot 5H_2O$ (1.0 mmol), sodium ascorbate (5.1 mmol) and 1-heptyne (25.5 mmol). The crude mixture was purified by silica chromatography (Pet. Ether/EtOAc, 4:1; $R_f$=0.27).

Yield: 64% (colourless liquid).

$^1$H NMR (400 MHz, $CDCl_3$): δ 7.22 (s, 1H), 4.26 (t, J=7.3 Hz, 2H), 2.69-2.60 (m, 2H), 1.82 (p, J=7.4 Hz, 2H), 1.61 (p, J=7.4 Hz, 2H), 1.37-1.21 (m, 6H), 0.89 (t, J=7.4 Hz, 3H), 0.88-0.80 (m, 3H).

$^{13}$C NMR (101 MHz, $CDCl_3$): δ 148.30, 120.32, 49.78, 32.27, 31.40, 29.14, 25.61, 22.35, 19.66, 13.93, 13.40.

HRMS (ESI+) m/z: $[C_{11}H_{21}N_3+H]^+$ calculated 196.18082. found 196.18098.

1.5 Synthesis of 1,4-butyl-1H-1,2,3-triazole (2)

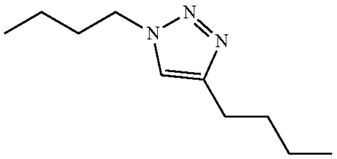

Synthesised from General Procedure A; 2 (2.33 g, 12.9 mmol, 75%) was obtained starting from sodium azide (25.6 mmol), 1-bromobutane (17.1 mmol), $CuSO_4·5H_2O$ (1.0 mmol), sodium ascorbate (5.1 mmol) and 1-hexyne (25.5 mmol). The crude mixture was purified by silica chromatography (Pet. Ether/EtOAc, 4:1; $R_f$=0.19).

Yield: 75% (colourless liquid).

$^1$H NMR (400 MHz, $CDCl_3$): δ 7.22 (s, 1H), 4.25 (t, J=7.2 Hz, 2H), 2.65 (t, J=7.8 Hz, 2H), 1.81 (p, J=7.4 Hz, 2H), 1.59 (p, J=7.6 Hz, 2H), 1.38-1.23 (m, 4H), 0.93-0.83 (m, 6H).

$^{13}$C NMR (101 MHz, $CDCl_3$): δ 148.25, 120.33, 49.78, 32.26, 31.55, 25.31, 22.25, 19.65, 13.74, 13.39.

HRMS (ESI+) m/z: $[C_{10}H_{19}N_3+H]^+$ calculated 182.16517. found 182.16539.

1.6. Synthesis of 4-Butyl-1H-1,2,3-Triazole-1-Acetic Acid Ethyl Ester (3)

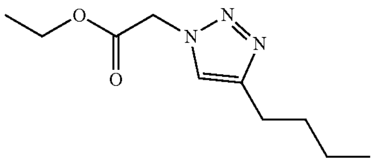

Synthesised from General Procedure A; 3 (1.99 g, 9.44 mmol, 56%) was obtained starting from sodium azide (25.5 mmol), ethyl bromoacetate (17.0 mmol), $CuSO_4·5H_2O$ (1.0 mmol), sodium ascorbate (6.0 mmol) and 1-hexyne (25.5 mmol). The crude mixture was purified by silica chromatography (Pet. Ether/EtOAc, 4:1; $R_f$=0.15).

Yield: 56% (white solid).

$^1$H NMR (400 MHz, $CDCl_3$): δ 7.38 (s, 1H), 5.07 (s, 2H), 4.19 (q, J=7.1 Hz, 2H), 2.68 (t, J=7.7 Hz, 2H), 1.61 (p, J=7.7 Hz, 2H), 1.33 (h, J=7.3 Hz, 2H), 1.23 (t, J=7.6 Hz, 3H), 0.87 (t, J=7.4 Hz, 3H).

$^{13}$C NMR (101 MHz, $CDCl_3$): δ 166.48, 148.71, 121.97, 62.17, 50.69, 31.36, 25.24, 22.17, 13.97, 13.72.

HRMS (ESI+) m/z: $[C_{10}H_{17}N_3O_2+H]^+$ calculated 212.13935. found 212.13977.

1.7 Synthesis of 1-butyl-4-(α,α-dimethyl methanol)-1H-1,2,3-triazole (4)

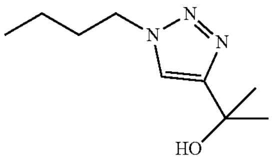

Synthesised from General Procedure A; 4 (3.12 g, 17.0 mmol, 100%) was obtained starting from sodium azide (25.4 mmol), 1-bromobutane (17.0 mmol), $CuSO_4·5H_2O$ (1.0 mmol), sodium ascorbate (5.8 mmol) and 2-methyl-3-butyne-2-ol (25.5 mmol). The crude mixture was purified by silica chromatography (Pet. Ether/EtOAc, 1:1; $R_f$=0.22).

Yield: quant. (yellow liquid).

$^1$H NMR (400 MHz, $CDCl_3$): δ 7.43 (s, 1H), 4.31 (t, J=7.3 Hz, 2H), 2.77 (s, 1H), 1.87 (p, J=7.4 Hz, 2H), 1.62 (s, 6H), 1.35 (h, J=7.4 Hz, 2H), 0.94 (t, J=7.4 Hz, 3H).

$^{13}$C NMR (101 MHz, $CDCl_3$): δ 155.49, 118.90, 68.46, 50.04, 32.24, 30.46, 19.72, 13.43.

HRMS (ESI+) m/z: $[C_9H_{17}N_{30}+H]^+$ calculated 184.14444. found 184.14458.

1.8 Synthesis of 4-butyl-1H-1,2,3-triazole-1-butanoic acid ethyl ester (5)

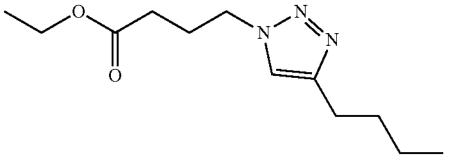 [SMILES: CCCCc1cn(CCCC(=O)OCC)nn1]

Synthesised from General Procedure A; 5 (1.08 g, 4.5 mmol, 56%) was obtained starting from sodium azide (8.0 mmol), ethyl 4-bromobutyrate (8.4 mmol), $CuSO_4·5H_2O$ (0.7 mmol), sodium ascorbate (4 mmol) and 1-hexyne (8.0 mmol). The crude mixture was purified by silica chromatography (Pet. Ether/EtOAc, 3:1; $R_f$=0.24).

Yield: 56% (pale yellow oil).

$^1$H NMR (400 MHz, $CDCl_3$): δ 7.24 (s, 1H), 4.34 (t, J=6.9 Hz, 2H), 4.08 (q, J=7.1 Hz, 2H), 2.65 (t, J=7.7 Hz, 2H), 2.28 (t, J=7.1 Hz, 2H), 2.15 (p, J=6.9 Hz, 2H), 1.59 (p, J=7.6 Hz, 2H), 1.33 (h, J=7.4 Hz, 2H), 1.20 (t, J=7.1 Hz, 3H), 0.87 (t, J=7.4 Hz, 3H).

$^{13}$C NMR (101 MHz, $CDCl_3$): δ 172.32, 148.43, 120.62, 60.60, 48.95, 31.50, 30.70, 25.46, 25.28, 22.24, 14.12, 13.75.

HRMS (ESI+) m/z: $[C_{12}H_{21}O_2N_3+H]^+$ calculated 240.17065. found 240.17061.

1.9 Synthesis of Substituted Triazoles 6-8 Via Phthalimide-Protected Intermediates Scheme 3: Reaction scheme for the synthesis of triazole 6.

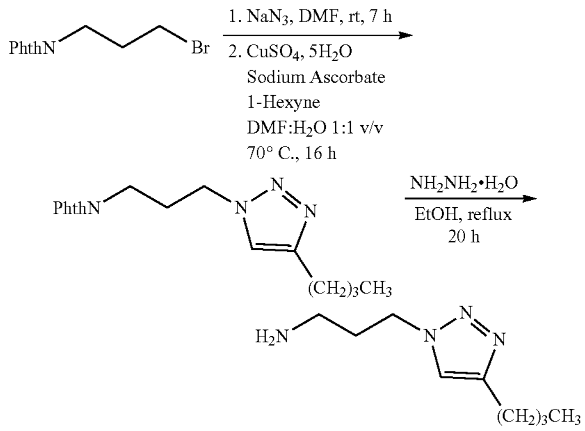

N006

1.10 Synthesis of 4-butyl-1H-1,2,3-triazole-1-propanamine (6)

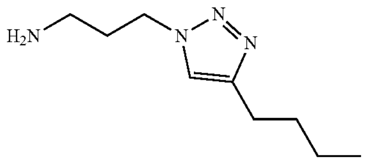

Synthesised from modified reported procedures (Pyta, K., et al., *European Journal of Medicinal Chemistry* 2014, 84, 651; Wang, Y.-F., et al., *Organic Letters* 2013, 15(11), 2842). N-(3-Bromopropyl)phthalimide (10.1 mmol) and sodium azide (15.2 mmol) were dissolved in DMF (26 mL) under argon and stirred at room temperature for 7 hrs. The reaction was diluted with $H_2O$ (26 mL) before the addition of $CuSO_4 \cdot 5H_2O$ (1.0 mmol), sodium ascorbate (5.3 mmol) and 1-hexyne (25.5 mmol) in succession. The reaction was heated at 70° C. with vigorous stirring.

The reaction was cooled to room temperature after 16 hours, before being diluted with $H_2O$ (80 mL) and extracted with ethyl acetate (3×80 mL). The extracts were combined, concentrated and purified by silica chromatography (Pet. Ether/EtOAc, 2:3; $R_f$=0.33). If crude failed to solidify due to remaining DMF, the sample was treated with 5% aq. LiCl solution to cause precipitation of 2-[3-(4-butyl-1H-1,2,3-triazol-1-yl)propyl]-1H-isoindole-1,3(2H)-dione as a cream powder (84%).

$^1$H NMR (400 MHz, $CDCl_3$): δ 7.89-7.80 (m, 2H), 7.78-7.68 (m, 2H), 7.44 (s, 1H), 4.36 (t, J=6.9 Hz, 2H), 3.74 (t, J=6.5 Hz, 2H), 2.68 (t, J=7.7 Hz, 2H), 2.31 (p, J=6.8 Hz, 2H), 1.63 (p, J=7.4 Hz, 2H), 1.37 (h, J=7.4 Hz, 2H), 0.92 (t, J=7.4 Hz, 3H).

$^{13}$C NMR (101 MHz, $CDCl_3$): δ 168.29, 148.41, 134.17, 131.87, 123.36, 121.00, 47.58, 35.11, 31.53, 29.44, 25.33, 22.30, 13.81.

HRMS (ESI+) m/z: $[C_{17}H_{20}N_4O_2+H]^+$ calculated 313.16590. found 313.16592.

2-[3-(4-Butyl-1H-1,2,3-triazol-1-1)propyl]-1H-isoindole-1,3(2H)-dione (8.5 mmol) was dissolved in ethanol (0.06 M) before being treated with hydrazine monohydrate (12.67 mmol). The solution was stirred vigorously and heated to 90° C. After heating overnight, a white precipitate had formed. The reaction was cooled, and the precipitate was removed by filtration and washed thoroughly. The filtrate was concentrated, and the resulting solid was resuspended in $CH_2Cl_2$ and filtered again. The filtrate was concentrated to a yellow oil which was purified by silica chromatography ($CH_2Cl_2$/MeOH/30% aq. $NH_3$, 10:1:0.1; $R_f$=0.16) to give 6 as a cream solid (1.01 g, 5.5 mmol, 65%).

Yield: 65% (cream solid).

$^1$H NMR (400 MHz, DMSO-$d_6$): δ 7.80 (s, 1H), 4.33 (t, J=7.0 Hz, 2H), 2.57 (t, J=7.6 Hz, 2H), 2.47 (t, J=6.6 Hz, 2H), 1.82 (p, J=6.8 Hz, 2H), 1.64-1.44 (m, 4H), 1.29 (h, J=7.3 Hz, 2H), 0.87 (t, J=7.4 Hz, 3H).

$^{13}$C NMR (101 MHz, DMSO-$d_6$): δ 147.17, 122.06, 47.40, 38.88, 34.08, 31.60, 25.14, 22.12, 14.10.

HRMS (ESI+) m/z: $[C_9H_{18}N_4+H]^+$ calculated 183.16042. found 183.16057.

Scheme 4: Reaction scheme for the synthesis of triazoles 7 and 8.

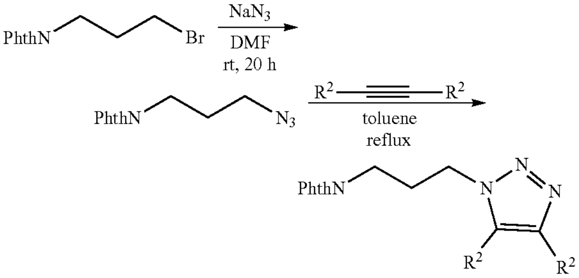

N007: $R^2 = CH_2OH$
N008: $R^2 = CH_2OC(O)CH_3$

1.11 Synthesis of 2-[3-[4,5-di(hydroxymethyl)-1H-1,2,3-triazole]propyl]-isoindoline-1,3-dione (7)

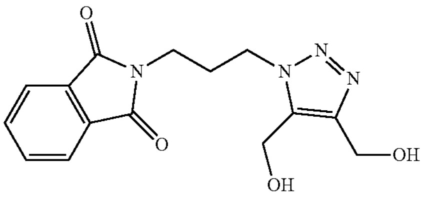 [SMILES: O=C1c2ccccc2C(=O)N1CCCn1nnc(CO)c1CO]

Sodium azide (9.4 mmol) was suspended in DMF (26 mL) under argon, and to this solution N-(3-bromopropyl)phthalimide (8.7 mmol) was added. The mixture was stirred at room temperature overnight. The reaction was then diluted slowly with $H_2O$ (100 mL), before extraction with ether. Concentration of the ethereal extracts provided N-(3-azidopropyl)phthalimide as a waxy cream solid (1.83 g, 7.94 mmol, 92%).

$^1$H NMR (400 MHz, $CDCl_3$): δ 7.90-7.79 (m, 2H), 7.77-7.67 (m, 2H), 3.78 (t, J=6.8 Hz, 2H), 3.38 (t, J=6.7 Hz, 2H), 1.96 (p, J=6.8 Hz, 2H).

$^{13}$C NMR (101 MHz, $CDCl_3$): δ 168.25, 134.04, 132.00, 123.31, 49.04, 35.38, 28.03.

HRMS (ESI+) m/z: $[C_{11}H_{10}O_2N_4+H]^+$ calculated 231.08765. found 231.08771.

N-(3-azidopropyl)phthalimide (7.9 mmol) was suspended in toluene (0.2 M) before addition of 2-butyne-1,4-diol (8.7 mmol). The reaction was stirred vigorously and heated to 115° C. for 41 hrs. Toluene was evaporated and the crude solid was recrystallised from $H_2O$ to give 7 as a white powder (1.34 g, 4.3 mmol, 54%).

Yield: 54% (white powder).

$^1$H NMR (400 MHz, DMSO-$d_6$): δ 7.89-7.77 (m, 4H), 5.29 (t, J=5.4 Hz, 1H), 5.01 (t, J=5.6 Hz, 1H), 4.57 (d, J=5.3 Hz, 2H), 4.46 (d, J=5.5 Hz, 2H), 4.37 (t, J=7.3 Hz, 2H), 3.65 (t, J=7.0 Hz, 2H), 2.18 (p, J=7.2 Hz, 2H).

$^{13}$C NMR (101 MHz, DMSO-$d_6$): δ 168.36, 145.05, 134.76, 134.52, 132.16, 123.44, 54.63, 51.10, 45.99, 35.69, 28.88.

HRMS (ESI+) m/z: $[C_{15}H_{16}O_4N_4+H]^+$ calculated 317.12443. found 317.12448.

1.12 Synthesis of 2-[3-[4,5-(methyl ethanoate)-1H-1,2,3-triazole]propyl]-isoindoline-1,3-dione (8)

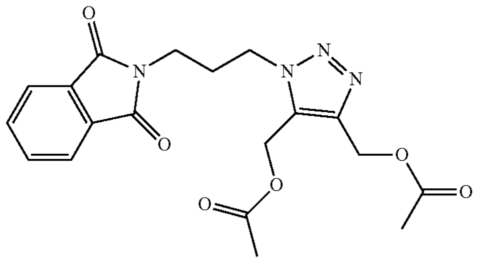 [SMILES: CC(=O)OCc1nnn(CCCN2C(=O)c3ccccc3C2=O)c1COC(C)=O]

As for 7, using 2-butyne-1,4-diol diacetate as alkyne, and the crude product was recrystallised from ethanol to give 8 as white crystals (3.69 g, 9.23 mmol, 71%).

Yield: 71% (white crystals).

$^1$H NMR (400 MHz, $CDCl_3$): δ 7.89-7.80 (m, 2H), 7.78-7.69 (m, 2H), 5.23 (s, 2H), 5.22 (s, 2H), 4.46-4.37 (m, 2H), 3.82 (t, J=6.7 Hz, 2H), 2.36 (p, J=6.9 Hz, 2H), 2.06 (s, 3H), 2.04 (s, 3H).

$^{13}$C NMR (101 MHz, $CDCl_3$): δ 170.67, 170.02, 168.20, 142.09, 134.17, 131.89, 130.65, 123.36, 56.67, 52.64, 46.51, 35.23, 29.09, 20.82, 20.50.

HRMS (ESI+) m/z: $[C_{19}H_{20}N_4O_6+H]^+$ calculated 401.14556. found 401.14563.

1.13 Synthesis of ethyl 4,5-bis(hydroxymethyl)-1H-1,2,3-triazole-1-butyrate (9)

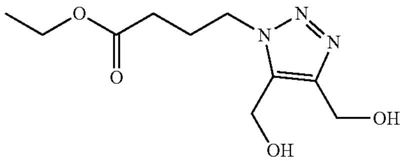 [SMILES: CCOC(=O)CCCn1nnc(CO)c1CO]

Synthesised from modified General Procedure B; 9 (1.21 g, 4.6 mmol, 33%) was obtained starting from sodium azide (22 mmol) and ethyl 4-bromobutyrate (19 mmol) heating in DMF (20 mL). The crude azide formed was treated with 2-butyne-1,4-diol (14 mmol) in toluene at 115° C. for 24 hrs. The crude mixture was purified by silica chromatography ($CH_2Cl_2/CH_3OH$, 10:0.6; $R_f$=0.28).

Yield: 33% (pale yellow oil).

$^1$H NMR (400 MHz, $CDCl_3$): δ 4.94 (s, 2H), 4.67 (s, 2H), 4.58 (s, 2H), 4.37 (t, J=7.1 Hz, 2H), 4.06 (q, J=7.1 Hz, 2H), 2.32 (t, J=7.1 Hz, 2H), 2.16 (p, J=7.1 Hz, 2H), 1.20 (t, J=7.1 Hz, 3H).

$^{13}$C NMR (101 MHz, $CDCl_3$): δ 172.65, 144.67, 134.23, 60.73, 55.06, 51.82, 47.53, 30.77, 24.99, 14.10.

HRMS (ESI+) m/z: $[C_{10}H_{17}N_3O_4+H]^+$ calculated 244.12918. found 244.12921.

1.14. Synthesis of ethyl 4,5-bis(methyl ethanoate)-1H-1,2,3-triazole-1-butyrate (10)

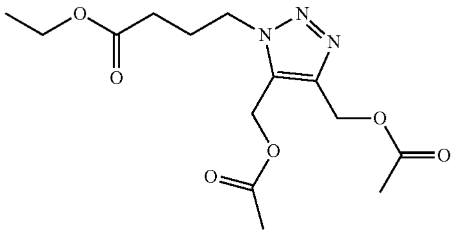 [SMILES: CCOC(=O)CCCn1nnc(COC(C)=O)c1COC(C)=O]

Synthesised from General Procedure B; 10 (2.5 g, 7.7 mmol, 74%) was obtained from sodium azide (15.8 mmol), ethyl 4-bromobutyrate (10.5 mmol) and 2-butyne-1,4-diol (11.1 mmol). The crude mixture was purified by silica chromatography (Pet. Ether/EtOAc, 3:2; $R_f$=0.1).

Yield: 74% (colourless oil).

$^1$H NMR (400 MHz, $CDCl_3$): δ 5.24 (s, 2H), 5.23 (s, 2H), 4.42 (t, J=7.1 Hz, 2H), 4.11 (q, J=7.1 Hz, 2H), 2.39 (t, J=7.0 Hz, 2H), 2.22 (p, J=7.1 Hz, 2H), 2.06 (s, 3H), 2.05 (s, 3H), 1.24 (t, J=7.1 Hz, 3H).

$^{13}$C NMR (101 MHz, $CDCl_3$): δ 172.24, 170.65, 170.01, 142.06, 130.64, 60.71, 56.71, 52.69, 47.65, 30.73, 25.15, 20.80, 20.56, 14.15.

HRMS (ESI+) m/z: $[C_{14}H_{21}N_3O_6+H]^+$ calculated 328.15031. found 328.15021.

1.15 Synthesis of ethyl 4,5-bis(methyl ethanoate)-1H-1,2,3-triazole-1-acetate (11)

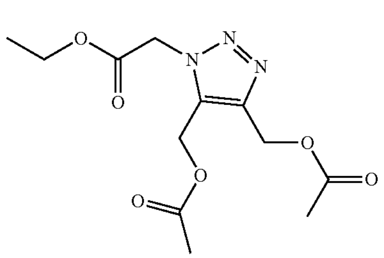 [SMILES: CCOC(=O)Cn1nnc(COC(C)=O)c1COC(C)=O]

Synthesised from General Procedure B; 11 (1.9 g, 6.3 mmol, 63%) was obtained from sodium azide (15.1 mmol), ethyl-2-bromoacetate (10.0 mmol) and 2-butyne-1,4-diol diacetate (10.7 mmol). The crude mixture was purified by silica chromatography (Pet. Ether/EtOAc, 1:1; $R_f$=0.43).

Yield: 63% (pale yellow oil).

$^1$H NMR (400 MHz, $CDCl_3$): δ 5.25 (s, 2H), 5.24 (s, 2H), 5.23 (s, 2H), 4.24 (q, J=7.1 Hz, 2H), 2.06 (s, 3H), 2.03 (s, 3H), 1.29 (t, J=7.1 Hz, 3H).

$^{13}C$ NMR (101 MHz, $CDCl_3$): δ 170.68, 170.16, 166.23, 142.21, 131.79, 62.50, 56.60, 52.97, 49.78, 20.81, 20.48, 14.04.

HRMS (ESI+) m/z: $[C_{12}H_{17}N_3O_6+H]^+$ calculated 300.11901. found 300.11890.

1.16. Synthesis of ethyl 4,5-bis(hydroxymethyl)-1H-1,2,3-triazole-1-acetate (12)

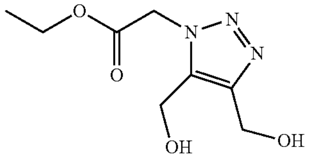

Synthesised from a reported procedure (Wen, Y.-n., et al., *Nucleosides, Nucleotides and Nucleic Acids* 2016, 35(3), 147). 12 (0.85 g, 3.9 mmol, 33%) was obtained from sodium azide (14.3 mmol), ethyl-2-bromoacetate (13.5 mmol) and 2-butyne-1,4-diol (12.1 mmol). The crude mixture was purified by silica chromatography ($CH_2Cl_2/CH_3OH$, 10:1; $R_f$=0.13).

Yield: 33% (white solid).

$^1H$ NMR (400 MHz, DMSO-$d_6$): δ 5.34 (t, J=5.5 Hz, 1H), 5.31 (s, 2H), 5.08 (t, J=5.7 Hz, 1H), 4.57 (d, J=5.4 Hz, 2H), 4.50 (d, J=5.5 Hz, 2H), 4.15 (q, J=7.1 Hz, 2H), 1.20 (t, J=7.1 Hz, 3H).

$^{13}C$ NMR (101 MHz, DMSO-$d_6$): δ 167.58, 144.81, 135.15, 61.82, 54.61, 51.67, 49.70, 14.40.

HRMS (ESI+) m/z: $[C_8H_{13}N_3O_4+H]^+$ calculated 216.09788. found 216.09734.

1.17. Synthesis of 1-butyl-4-propyl-1H-1,2,3-triazole (13)

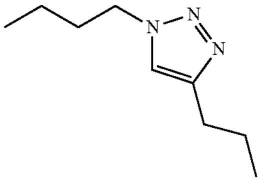

Synthesised from General Procedure A; 13 (2.55 g, 15.2 mmol, 89%) was obtained starting from sodium azide (20.3 mmol), 1-bromobutane (17.0 mmol), $CuSO_4·5H_2O$ (1.0 mmol), sodium ascorbate (5.2 mmol) and 1-pentyne (20.0 mmol). The crude mixture was purified by silica chromatography (Pet. Ether/EtOAc, 3:2; $R_f$=0.37).

Yield: 89% (colourless oil).

$^1H$ NMR (400 MHz, $CDCl_3$): δ 7.23 (s, 1H), 4.28 (t, J=7.2 Hz, 2H), 2.66 (t, J=7.6 Hz, 2H), 1.84 (p, J=7.3 Hz, 2H), 1.66 (h, J=7.4 Hz, 2H), 1.32 (h, J=7.4 Hz, 2H), 0.96-0.89 (m, 6H).

$^{13}C$ NMR (101 MHz, $CDCl_3$): δ 148.11, 120.38, 49.82, 32.29, 27.66, 22.70, 19.68, 13.74, 13.43.

HRMS (ESI+) m/z: $[C_9H_{17}N_3+H]^+$ calculated 168.14952. found 168.14951.

1.18 Synthesis of 1-(2-methoxyethyl)-4-butyl-1H-1,2,3-triazole (14)

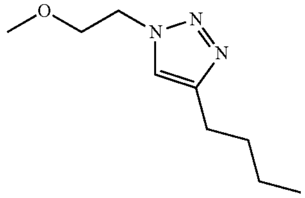

14 (0.75 g, 4.1 mmol, 65%) was obtained from purified 15 (6.3 mmol) dissolved in dry THF (42 mL) under argon, cooled to 0° C. NaH (6.6 mmol) was added in a single portion. Once gas evolution had ceased, MeI (9.5 mmol) was added in three portions the mixture stirred at room temperature for 24 hours. The reaction was diluted with $H_2O$ and THF was removed in vacuo. The product was extracted into ethyl acetate and concentrated. The crude mixture was purified by silica chromatography (Pet. Ether/EtOAc, 1:1; $R_f$=0.21).

Yield: 65% (colourless oil).

$^1H$ NMR (400 MHz, $CDCl_3$): δ 7.36 (s, 1H), 4.45 (t, J=5.0 Hz, 2H), 3.71 (t, J=5.0 Hz, 2H), 3.32 (s, 3H), 2.68 (t, J=7.8 Hz, 2H), 1.63 (p, J=7.8 Hz, 2H), 1.36 (h, J=7.3 Hz, 2H), 0.90 (t, J=7.4 Hz, 3H).

$^{13}C$ NMR (101 MHz, $CDCl_3$): δ 148.26, 121.61, 70.91, 58.93, 50.06, 31.52, 25.31, 22.29, 13.78.

HRMS (ESI+) m/z: $[C_9H_{17}N_{30}+H]^+$ calculated 184.14444. found 184.14445.

1.19 Synthesis of 4-propyl-1H-1,2,3-triazole-1-ethanol (15)

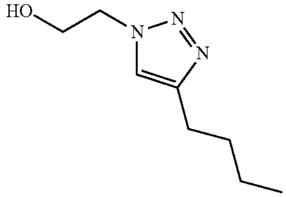

Synthesised from General Procedure A; 15 (1.06 g, 6.3 mmol, 36%) was obtained starting from sodium azide (26.2 mmol), 2-bromoethanol (17.5 mmol), $CuSO_4·5H_2O$ (1.0 mmol), sodium ascorbate (5.6 mmol) and 1-hexyne (25.5 mmol). The crude mixture was purified by silica chromatography (Pet. Ether/EtOAc, 2:3; $R_f$=0.1).

Yield: 36% (pale yellow liquid).

$^1H$ NMR (400 MHz, $CDCl_3$): δ 7.41 (s, 1H), 4.70 (s, 1H), 4.37 (t, J=5.2 Hz, 2H), 3.95 (t, J=5.1 Hz, 2H), 2.62-2.53 (m, 2H), 1.54 (p, J=7.4 Hz, 2H), 1.29 (h, J=7.3 Hz, 2H), 0.85 (t, J=7.4 Hz, 3H).

$^{13}C$ NMR (101 MHz, $CDCl_3$): δ 147.87, 121.99, 60.71, 52.62, 31.36, 25.11, 22.20, 13.73.

HRMS (ESI+) m/z: $[C_8H_{15}N_{30}+H]^+$ calculated 170.12879. found 170.12887.

1.20. Synthesis of 1,4-dipropyl-1H-1,2,3-triazole (16)

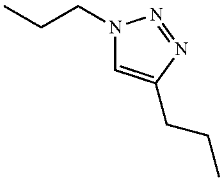

Synthesised from General Procedure A, 16 (0.68 g, 4.36 mmol, 26%) was obtained starting from sodium azide (20.0 mmol), 1-bromopropane (17.0 mmol), $CuSO_4·5H_2O$ (1.0 mmol), sodium ascorbate (5.1 mmol) and 1-pentyne (20.1 mmol). The crude mixture was purified by silica chromatography (Pet. Ether/EtOAc, 2:1; $R_f$=0.23).

Yield: 26% (colourless oil).

$^1H$ NMR (400 MHz, $CDCl_3$): δ 7.24 (s, 1H), 4.25 (t, J=7.2 Hz, 2H), 2.66 (t, J=7.5 Hz, 2H), 1.89 (h, J=7.3 Hz, 2H), 1.66 (h, J=7.4 Hz, 2H), 0.96-0.89 (m, 6H).

$^{13}C$ NMR (101 MHz, $CDCl_3$): δ 148.10, 120.46, 51.71, 27.64, 23.72, 22.70, 13.74, 11.04.

HRMS (ESI+) m/z: $[C_8H_{15}N_3+H]^+$ calculated 154.13387. found 154.13385.

1.21. Synthesis of 1-(3-butyn-1-yl)-4-propyl-1H-1,2,3-triazole (17)

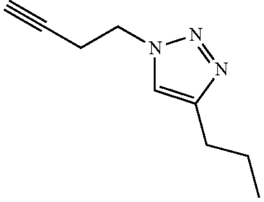

Synthesised from a modified General Procedure A. 17 (0.30 g, 1.8 mmol, 18%) was obtained from sodium azide (15.0 mmol) and 1-bromobutyne (10.0 mmol) heating at 60° C. in DMF (15 mL) for 3 hours. The reaction was cooled and diluted with $H_2O$ (15 mL), followed by addition of $CuSO_4·5H_2O$ (1.2 mmol), sodium ascorbate (2.0 mmol) and 1-pentyne (17.9 mmol). The reaction was stirred at room temperature overnight. The crude mixture was purified by silica chromatography (Pet. Ether/Diethyl Ether, 2:1; $R_f$=0.17).

Yield: 18% (pale yellow oil).

$^1H$ NMR (400 MHz, $CDCl_3$): δ 7.39 (s, 1H), 4.46 (t, J=6.7 Hz, 2H), 2.76 (td, J=6.7, 2.6 Hz, 2H), 2.68 (t, J=7.6 Hz, 2H), 2.05 (t, J=2.6 Hz, 1H), 1.68 (h, J=7.4 Hz, 2H), 0.95 (t, J=7.4 Hz, 3H).

$^{13}C$ NMR (101 MHz, $CDCl_3$): δ 148.14, 121.10, 79.69, 71.32, 48.53, 27.60, 22.66, 20.65, 13.72.

HRMS (ESI+) m/z: $[C_9H_{13}N_3+H]^+$ calculated 164.11822. found 164.11824.

1.22. Synthesis of 1-(2-propen-1-yl)-4-propyl-1H-1,2,3-triazole (18)

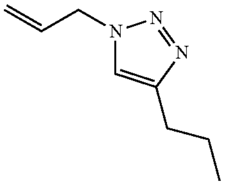

Synthesised from a modified General Procedure A. 18 (1.77 g, 11.7 mmol, 78%) was obtained from sodium azide (21.0 mmol), allyl bromide (15.0 mmol), $CuSO_4·5H_2O$ (0.9 mmol), sodium ascorbate (4.5 mmol) and 1-pentyne (21.0 mmol), heated overnight at 45° C. The crude mixture was purified by silica chromatography (Pet. Ether/EtOAc, 4:1; $R_f$=0.13).

Yield: 78% (colourless oil).

$^1H$ NMR (400 MHz, $CDCl_3$): δ 7.26 (s, 1H), 6.08-5.93 (m, 1H), 5.37-5.27 (m, 1H), 5.33-5.20 (m, 1H), 4.94 (dt, J=6.1, 1.4 Hz, 2H), 2.69 (t, J=7.6 Hz, 2H), 1.69 (h, J=7.4 Hz, 2H), 0.96 (t, J=7.3 Hz, 3H).

$^{13}C$ NMR (101 MHz, $CDCl_3$): δ 148.50, 131.58, 120.39, 119.73, 52.54, 27.69, 22.70, 13.75.

HRMS (ESI+) m/z: $[C_8H_{13}N_3+H]^+$ calculated 152.1182. found 152.1183.

1.23. Synthesis of ethyl 2-(4-propyl-1H-1,2,3-triazol-1-yl)-acetate (19)

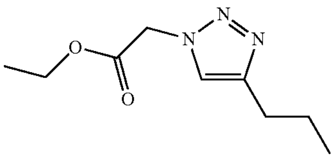

Synthesised from General Procedure A; 19 (2.83 g, 14.4 mmol, 85%) was obtained from sodium azide (20 mmol), ethyl bromoacetate (17.1 mmol), $CuSO_4·5H_2O$ (1.0 mmol), sodium ascorbate (5.1 mmol) and 1-pentyne (20 mmol), heated at 50° C. for 9 hrs. Following workup, the crude mixture was purified by silica chromatography (Pet. Ether/EtOAc, 1:1; $R_f$=0.27).

Yield 85% (cream waxy solid)

$^1H$ NMR (400 MHz, $CDCl_3$): δ 7.41 (s, 1H), 5.11 (s, 2H), 4.24 (q, J=7.2 Hz, 2H), 2.71 (t, J=7.6 Hz, 2H), 1.70 (h, J=7.4 Hz, 2H), 1.28 (t, J=7.1 Hz, 3H), 0.96 (t, J=7.4 Hz, 3H).

$^{13}C$ NMR (101 MHz, $CDCl_3$): δ 166.44, 148.62, 122.02, 62.28, 50.77, 27.58, 22.55, 14.03, 13.69.

HRMS (ESI+) m/z: $[C_9H_{15}N_3O_2+H]^+$ calculated 198.12370. found 198.12385.

1.24. Synthesis of prop-2-en-1-yl 2-(4-propyl-1H-1,2,3-triazol-1-yl)-acetate (20)

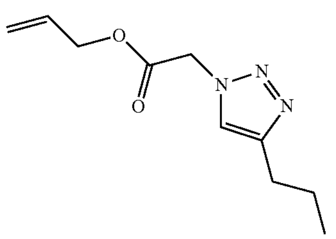

19 was saponified to the corresponding acid following the procedure reported in Sabbah et al. (Sabbah, M., et al., *Bioorganic & Medicinal Chemistry,* 2012, 20(15), 4727-4736) with ethanolic KOH. The resulting acid (1.9 mmol), 4-dimethylaminopyridine (0.2 mmol) and allyl alcohol (4.4 mmol) were combined in dichloromethane (15 mL) under argon. After stirring for 30 minutes, the solution was cooled to 0° C. before adding N,N'-dicyclohexylcarbodiimide (2 mmol). The solution was stirred at room temperature for 24 hours and then filtered and concentrated in vacuo. The residue was resuspended in ethyl acetate and filtered again. The filtrate was concentrated to an oil, which was purified by silica chromatography (Pet. Ether/EtOAc, 1:1, $R_f$=0.33).

Yield 70% (white waxy solid)

$^1$H NMR (400 MHz, $CDCl_3$): δ 7.42 (s, 1H), 5.97-5.82 (m, 1H), 5.38-5.24 (m, 2H), 5.15 (s, 2H), 4.72-4.64 (m, 2H), 2.72 (t, J=7.6 Hz, 2H), 1.71 (h, J=7.3 Hz, 2H), 0.97 (t, J=7.3 Hz, 3H).

$^{13}$C NMR (101 MHz, $CDCl_3$): δ 166.15, 148.67, 130.83, 122.02, 119.62, 66.68, 50.72, 27.58, 22.56, 13.71.

HRMS (ESI+) m/z: $[C_{10}H_{15}N_3O_2+H]^+$ calculated 210.12370. found 210.12392.

1.25. Synthesis of prop-2-en-1-yl 2-(4-propyl-1H-1,2,3-triazol-1-yl)-acetamide (21)

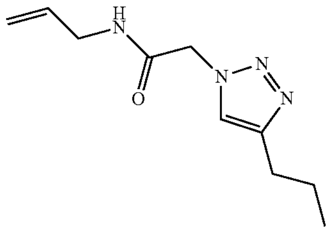

19 was saponified to the corresponding acid following the procedure reported in Sabbah et al. (Sabbah, M., et al., *Bioorganic & Medicinal Chemistry,* 2012, 20(15), 4727-4736) with ethanolic KOH. The resulting acid (1.8 mmol) was dissolved in dichloromethane/dimethylformamide (20 mL/2.5 mL) under argon, and treated with HOBt (4.0 mmol), N-(3-dimethylaminopropyl)-N'-ethylcarbodiimide hydrochloride (4.0 mmol) and allyl amine (4.0 mmol). After stirring for 10 hrs at room temperature, the mixture was treated with 5 drops of acetic acid and washed with $H_2O$ and brine. The crude product was purified by silica chromatography ($CH_2Cl_2$/MeOH, 100:1 to 100:5 gradient, $R_f$=0.1).

Yield 56% (cream solid).

$^1$H NMR (400 MHz, $CDCl_3$): δ 7.46 (s, 1H), 6.43 (s, 1H), 5.83-5.69 (m, 1H), 5.14-5.07 (m, 2H), 5.05 (s, 2H), 3.91-3.82 (m, 2H), 2.71 (t, J=7.6 Hz, 2H), 1.71 (h, J=7.4 Hz, 2H), 0.97 (t, J=7.4 Hz, 3H).

$^{13}$C NMR (101 MHz, $CDCl_3$): δ 165.15, 148.87, 133.01, 122.53, 116.89, 53.07, 42.00, 27.47, 22.49, 13.72.

HRMS (ESI+) m/z: $[C_{10}H_{16}N_4O+H]^+$ calculated 209.13969. found 209.13990.

1.26. Synthesis of prop-2-yn-1-yl 2-(4-propyl-1H-1,2,3-triazol-1-yl)-acetate (22)

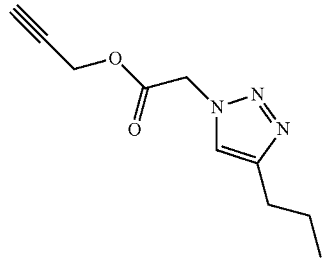

19 was saponified to the corresponding acid following the procedure reported in Sabbah et al. (Sabbah, M., et al., *Bioorganic & Medicinal Chemistry,* 2012, 20(15), 4727-4736) with ethanolic KOH. The resulting acid (1.8 mmol), 4-dimethylaminopyridine (0.4 mmol) and propargyl alcohol (3.4 mmol) were combined in dichloromethane (15 mL) under argon. After stirring for 30 minutes, the solution was cooled to 0° C. and N,N'-dicyclohexylcarbodiimide (1.9 mmol) was added. The mixture was stirred at room temperature for 24 hours, filtered and concentrated in vacuo. The residue was resuspended in ethyl acetate and filtered again. The filtrate was concentrated to an oil, which was purified by silica chromatography (Pet. Ether/EtOAc, 1:1, $R_f$=0.33).

Yield 71% (colourless liquid)

$^1$H NMR (400 MHz, $CDCl_3$): δ 7.43 (s, 1H), 5.19 (s, 2H), 4.79 (d, J=2.5 Hz, 2H), 2.72 (t, J=7.6 Hz, 2H), 2.53 (t, J=2.4 Hz, 1H), 1.71 (h, J=7.4 Hz, 2H), 0.97 (t, J=7.4 Hz, 3H).

$^{13}$C NMR (101 MHz, $CDCl_3$): δ 165.77, 148.74, 122.06, 76.30, 76.07, 53.45, 50.52, 27.55, 22.53, 13.71.

HRMS (ESI+) m/z: $[C_{10}H_{13}N_3O_2+H]^+$ calculated 208.10805. found 208.10828.

1.27. Synthesis of prop-2-yn-1-yl 2-(4-propyl-1H-1,2,3-triazol-1-yl)-acetamide (23)

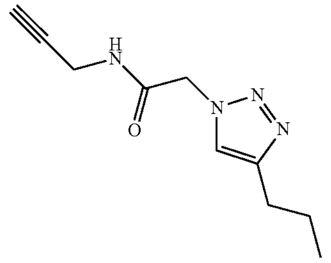

19 was saponified to the corresponding acid following the procedure reported in Sabbah et al. (Sabbah, M., et al., *Bioorganic & Medicinal Chemistry,* 2012, 20(15), 4727-4736) with ethanolic KOH. The resulting acid (1.8 mmol) was dissolved in dichloromethane/dimethylformamide (20 mL/2.5 mL) under argon, and treated with HOBt (3.7 mmol), EDCl (4.0 mmol) and allyl amine (3.5 mmol). After stirring for 10 hrs at room temperature, the mixture was treated with 5 drops of acetic acid and washed with $H_2O$ and brine. The crude product was purified by silica chromatography ($CH_2Cl_2$/MeOH, 100:1 to 100:5 gradient, $R_f$=0.1).

Yield 61% (cream solid)

$^1$H NMR (400 MHz, $CDCl_3$): δ 7.47 (s, 1H), 6.79-6.71 (m, 1H), 5.06 (s, 2H), 4.04 (dd, J=5.4, 2.5 Hz, 2H), 2.71 (t, J=7.6 Hz, 2H), 2.21 (t, J=2.6 Hz, 1H), 1.71 (h, J=7.4 Hz, 2H), 0.97 (t, J=7.4 Hz, 3H).

$^{13}$C NMR (101 MHz, $CDCl_3$): δ 165.04, 148.87, 122.60, 78.45, 72.03, 52.84, 29.38, 27.47, 22.48, 13.73.

HRMS (ESI+) m/z: $[C_{10}H_{14}N_4O+H]^+$ calculated 207.12404. found 207.12411.

2. Soil Experiments

The soil used in this study was collected from four different locations in Victoria, Australia: (i) a wheat cropping soil from Horsham (36°45' S, 142°07' E), (ii) a rotational cropping soil from Dahlen (36°37' S, 142°09' E), (iii) a vegetable growing soil from Clyde (38°08' S, 145°20' E), and (iv) a pasture soil from Terang (38°15'S, 142°52'E). In addition, a sugarcane cropping soil from South Johnstone in northern Queensland (17°34' S, 145°57' E) was also studied. The water content of the soil was calculated before commencing each experiment, from samples that were oven-dried to constant weight. The soil's water-filled pore space (WFPS) was in the range 52%-61%, which is within the recommended 50-70% range for microbial activity due to oxygen and nutrient availability (Fichtner, T., et al., *Applied Sciences,* 2019, 9, 496).

The pH values and residual (initial) concentrations of ammonium-N and nitrate-N in the tested soils are compiled in Table 1 below.

3,4-Dimethylpyrazole phosphate (DMPP), prepared as a solution of 3,4-dimethylpyrazole in phosphoric acid, was obtained from Incitec Pivot Fertilisers.

TABLE 1

Residual concentrations of ammonium-N and nitrate-N and pH of the soils tested in this study

| | Baseline (mg kg$^{-1}$) | | | pH |
|---|---|---|---|---|
| Soil Location | $NH_4^+$—N | $NO_3^-$—N | Organic Carbon (%) | (1:5 water) |
| South Johnstone | 14 | 15 | 1.21 | 5.0 |
| Terang | 29 | 27 | 4.6 | 6.5 |
| Clyde | 2 | 48 | 1.9 | 7.2 |
| Dahlen | 3.3 | 270 | 1.02 | 7.3 |
| Horsham | 0.95 | 7.2 | 0.73 | 8.8 |

2.1. Soil Incubation Experiments

Soil microcosm incubations were carried out in 250 ml polypropylene specimen containers (Sarstedt, Germany), containing 18.24 g oven dry-weight equivalent of soil. Microcosms were re-wetted and pre-incubated at the test temperature for seven days to revive soil microbial activity. Following pre-incubation, the remaining volume to reach the desired water-filled pore spaces (WFPS %) was applied as one of the following treatment solutions; $(NH_4)_2SO_4$ (Control), $(NH_4)_2SO_4$+DMPP, or $(NH_4)_2SO_4$+one of Compounds 1-23. Each treatment was applied in triplicate per soil type, so that n=3 at each time point.

Treatment solutions were prepared such that each microcosm received $(NH_4)_2SO_4$ at a rate of 100 mg N per kg soil, Compounds 1-23 at 10 mol % of applied N, or DMPP at one of 1.5, 3.6 or 10 mol % of applied N, referred to as L-DMPP, M-DMPP or H-DMPP respectively.

The microcosms were incubated for 0, 3, 7, 14, 21 or 28 days, where day 0 samples were extracted following 1-hour incubation post-treatment. Soil microcosms were aerated and moisture levels were replenished based on weight loss every few days throughout the incubation period.

At the end of each incubation period, soil microcosms were destructively sampled by treatment with 2M KCl (100 mL). After shaking for 1 hour, soil-KCl solutions were filtered (Whatman 42) before storing the filtrates at −20° C. until the conclusion of the experiment. All KCl extracts were then analysed by Segmented Flow Analysis (San ++, Skalar, Breda, The Netherlands) for the concentration of nitrogen from ammonium ($NH_4^+$—N) and nitrogen from $NO_3$ and $NO_2$ ($NO_x^-$—N) after appropriate dilutions. Results are reported as the mean of three replicates, errors reported are standard errors of the mean.

2.1.2. Calculating Percent Nitrification and Percent Nitrification Inhibition

Nitrification calculations were performed as previously reported (Aulakh, M., et al., *Biology and Fertility of Soils* 2001, 33, 258-263; Mahmood, T., et al., *Soil Research* 2017, 55, 715-722) without correction for the initial baseline concentrations of $NH_4^+$—N or $NO_3^-$—N in the untreated soil. For each treatment nitrified $NH_4^+$—N (%) was calculated according to eqn. 1:

$$\text{nitrified } NH_4^+ - N(\%) = \frac{[NH_4^+ - N]_0 - [NH_4^+ - N]_t}{[NH_4^+ - N]_0} \times 100 \qquad \text{(eqn. 1)}$$

where $[NH_4^+—N]_0$ is the $NH_4^+$—N concentration (in mg N kg$^{-1}$ soil) of the soil on day 0 and $[NH_4^+—N]_t$ is the $NH_4^+$—N concentration (in mg N kg$^{-1}$ soil) of the soil at a given time point t.

$NO_x^-$—N accumulation rates (mg $NO_x^-$—N/kg soil/day) over the 28-day incubation experiments were calculated for each treatment as in the following (eqn. 2):

$$NO_x^- - N \text{ accumulation} = \frac{[NO_x^- - N]_{t=28} - [NO_x^- - N]_{t=0}}{28} \qquad \text{(eqn. 2)}$$

$[NO_x^-—N]_{t=0}$ and $[NO_x^-—N]_{t=28}$ are the combined concentrations of nitrite ($NO_2$) and nitrate ($NO_3$) in the soil (in mg N kg$^{-1}$ soil) on day 0 and day 28, respectively.

Nitrification inhibition (%) was calculated based on either $NH_4^+$—N data (i.e., the percent nitrified $NH_4^+$—N calculated from eqn. 1), or on $NO_x^-$—N data. For nitrification inhibition based on $NH_4^+$—N, percent values were calculated from the nitrified $NH_4^+$—N percentage of the fertilised control (only $(NH_4)_2SO_4$) at a given time point t, and the nitrified $NH_4^+$—N percentage in the treated sample ($(NH_4)_2SO_4$ and NI) at the same time point, according to eqn. 3:

$$\text{nitrification inhibition (\%) based on } NH_4^+ - N = \frac{[\text{nitrified } NH_4^+ - N(\%)]_{t,control} - [\text{nitrified } NH_4^+ - N(\%)]_{t,treated}}{|[\text{nitrified } NH_4^+ - N(\%)]_{t,control}|} \times 100 \quad \text{(eqn. 3)}$$

For nitrification inhibition based on $NO_x^-$—N concentrations, percent values were calculated from the $NO_x^-$—N concentrations in the fertilised control (only $(NH_4)_2SO_4$) at a given time point, t, and the $NO_x^-$—N concentrations in the treated sample ($(NH_4)_2SO_4$ and NI) at the same timepoint, according to eqn. 4:

$$\frac{[NO_x^- - N]_{t,control} - [NO_x^- - N]_{t,treated}}{[NO_x^- - N]_{t,control}} \times 100 \quad \text{(eqn. 4)}$$

2.1.3 Statistical Analysis

All data presented are means of three replicates. Statistical analyses were performed on raw $NH_4^+$—N and $NO_x$—N data in R (version 3.5.2; R Core Team, 2018), using the statistical package emmeans (Lenth, 2019). Data were assessed for statistical significance ($P<0.05$) via two-way analysis of variation (ANOVA; Chambers & Hastie, 1992) assessing the impact of the two factors "Day" and "Treatment", and pair-wise comparisons between treatments at each time point were evaluated using a TukeyHSD post-hoc adjustment. Statistical results for inhibitor treatments compared to both the fertilised control $(NH_4)_2SO_4$ treatment and DMPP treatment are illustrated in the tables displaying raw $NH_4^+$—N and $NO_x^-$—N data.

2.1.4. $NH_4^+$—N and $NO_x$—N Concentrations

Incubation tests of compounds compared to either low-concentration DMPP (1.5 mol %, L-DMPP) or medium-concentration DMPP (3.6 mol %, M-DMPP) treatments were conducted in all soils to obtain initial structure-activity relationship information to guide future synthesis. Selected compounds were re-tested along with Compounds 13 to 17 in the alkaline soils (Horsham, Dahlen) against high-concentration DMPP (10 mol %, H-DMPP) treatment. In most studies, the applied fertiliser $NH_4^+$—N had been completely consumed in the control $(NH_4)_2SO_4$ treatments within the 28 days. In general, the nitrification inhibitors were most effective at slowing $NO_x$—N production in the more alkaline soils (Horsham, Dahlen).

Terang Soil

In the acidic Terang soil, Compound 3 and L-DMPP were the most effective treatments at retaining more $NH_4^+$—N in the soil than the fertilised control (see Table 2 below). Reduced $NO_x^-$—N production was also observed for these treatments when compared to the fertilised control, predominantly until day 14 after which the concentrations converged to that of the control.

TABLE 2

Ammonia nitrified (%) during a 28-day incubation at 25° C. in Terang soil (pH 6.5). Emboldened values indicate nitrification rates lower than those observed in the control treatment ($(NH_4)_2SO_4$), correlating positively to inhibitor activity. Errors stated are standard errors of the mean, n = 3.

| | Nitrified $NH_4^+$—N (%) | | | |
|---|---|---|---|---|
| Treatment | Day 3 | Day 7 | Day 14 | Day 28 |
| $(NH_4)_2SO_4$ | 36.8 ± 7.4 | 72.7 ± 8.0 | 74.3 ± 7.4 | 94.3 ± 9.2 |
| $(NH_4)_2SO_4$ + 1 | 13.6 ± 3.1 | 43.1 ± 3.7 | 85.1 ± 4.5 | 100 ± 4.2 |
| $(NH_4)_2SO_4$ + 2 | 27.2 ± 2.0 | 64.8 ± 2.3 | 95.6 ± 2.8 | 100 ± 2.7 |
| $(NH_4)_2SO_4$ + 3 | 15.6 ± 3.0 | 29.4 ± 2.6 | 47.8 ± 3.5 | 99.9 ± 2.8 |
| $(NH_4)_2SO_4$ + 4 | 27.0 ± 7.5 | 67.3 ± 5.2 | 96.4 ± 5.8 | 100 ± 5.9 |
| $(NH_4)_2SO_4$ + L-DMPP | 23.5 ± 3.7 | 47.8 ± 2.0 | 89.6 ± 3.1 | 100 ± 2.5 |

Horsham Soil

As is evident from FIG. 1 and Table 3, of the various inhibitors tested at 25° C., Compounds 13, 16, 17 (and to a lesser extent Compound 2) performed statistically better at retaining $NH_4^+$ than the uninhibited control treatment after 28 days with $P<0.001$ for these compounds, except for Compound 2, and inhibiting $NO_x^-$ formation (P=0.013 (13), 0.001 (16), <0.001 (17)). At 35° C., all of Compounds 2, 13, 16 and 17 showed lower nitrification rates than the uninhibited control treatment. Of these, Compound 13 and DMPP performed statistically better at retaining $NH_4^+$ (P=0.004 (13) and 0.008 (DMPP) and preventing $NO_x^-$ production (P=0.03 for both treatments), with Compound 13 being slightly more efficient in retarding nitrification of ammonia than DMPP (61% vs 65% $NH_4^+$—N consumption, respectively).

TABLE 3

Ammonia nitrified (%) during a 28-day incubation at either 25° C. or 35° C. in Horsham soil (pH 8.8). Emboldened values indicate nitrification rates lower than those observed in the control treatment ($(NH_4)_2SO_4$), correlating positively to inhibitor activity. Errors stated are standard errors of the mean, n = 3.

| Test Temp | | Nitrified $NH_4^+$—N (%) | | | | |
|---|---|---|---|---|---|---|
| (° C.) | Treatment | Day 3 | Day 7 | Day 14 | Day 21 | Day 28 |
| 25 | $(NH_4)_2SO_4$ | 13.5 ± 8.4 | 68.5 ± 2.4 | 100 ± 2.7 | 100 ± 2.7 | 100 ± 2.7 |
| | $(NH_4)_2SO_4$ + 2 | 12.2 ± 8.6 | 17.9 ± 6.9 | 44.5 ± 7.2 | 66.6 ± 8.9 | 90.4 ± 9.7 |
| | $(NH_4)_2SO_4$ + 13 | 17.7 ± 3.9 | 23.4 ± 5.4 | 40.0 ± 4.3 | 47.2 ± 4.3 | 72.2 ± 4.8 |
| | $(NH_4)_2SO_4$ + 14 | 23.8 ± 3.0 | 38.7 ± 5.3 | 84.3 ± 5.6 | 93.4 ± 6.2 | 100 ± 3.2 |

TABLE 3-continued

Ammonia nitrified (%) during a 28-day incubation at either 25° C. or 35° C. in Horsham soil (pH 8.8). Emboldened values indicate nitrification rates lower than those observed in the control treatment ($(NH_4)_2SO_4$), correlating positively to inhibitor activity. Errors stated are standard errors of the mean, n = 3.

| Test Temp (° C.) | Treatment | Nitrified $NH_4^+$—N (%) Day 3 | Day 7 | Day 14 | Day 21 | Day 28 |
|---|---|---|---|---|---|---|
| | $(NH_4)_2SO_4$ + 16 | 8.9 ± 3.4 | 24.9 ± 3.0 | 44.2 ± 3.3 | 57.5 ± 3.4 | 70.9 ± 3.9 |
| | $(NH_4)_2SO_4$ + 17 | 13.5 ± 4.7 | 30.6 ± 5.5 | 35.1 ± 5.1 | 43.9 ± 5.7 | 65.8 ± 5.2 |
| | $(NH_4)_2SO_4$ + H-DMPP | −6.9 ± 2.8 | 8.5 ± 2.8 | 37.2 ± 2.3 | 75.7 ± 5.4 | 76.2 ± 2.1 |
| 35 | $(NH_4)_2SO_4$ | 18.8 ± 2.4 | 45.9 ± 1.7 | 81.6 ± 3.7 | 84.5 ± 11.0 | 98.0 ± 2.0 |
| | $(NH_4)_2SO_4$ + 2 | −3.3 ± 5.9 | 8.8 ± 5.5 | 40.3 ± 5.4 | 53.8 ± 9.4 | 71.6 ± 22.9 |
| | $(NH_4)_2SO_4$ + 13 | 3.5 ± 6.4 | 18.7 ± 5.5 | 48.0 ± 5.3 | 59.3 ± 10.3 | 61.2 ± 14.2 |
| | $(NH_4)_2SO_4$ + 14 | 13.2 ± 5.4 | 15.7 ± 5.7 | 39.8 ± 6.6 | 83.5 ± 7.2 | 79.7 ± 9.4 |
| | $(NH_4)_2SO_4$ + 16 | 2.5 ± 4.5 | 22.3 ± 4.3 | 42.3 ± 4.6 | 74.9 ± 6.1 | 83.7 ± 6.1 |
| | $(NH_4)_2SO_4$ + 17 | −0.8 ± 3.4 | 8.5 ± 2.8 | 37.2 ± 2.3 | 75.7 ± 5.4 | 76.2 ± 2.1 |
| | $(NH_4)_2SO_4$ + H-DMPP | 7.9 ± 3.0 | 18.9 ± 2.8 | 32.3 ± 4.1 | 46.6 ± 5.9 | 64.5 ± 12.7 |

Figure 2:
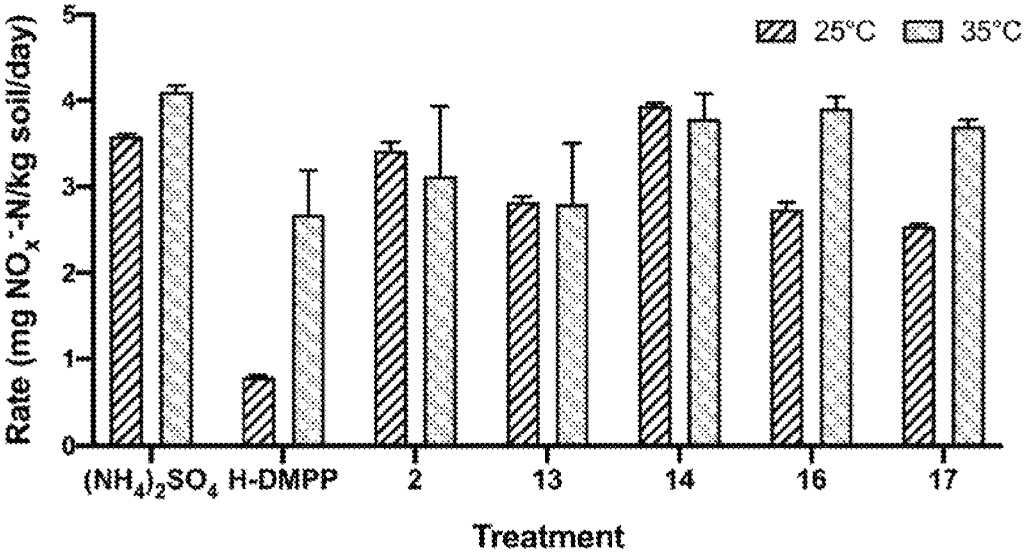
FIG. 2 illustrates calculated $NO_x^-$—N production rates (mg $NO_x^-$—N/kg soil/day) after 28-day incubation in the Horsham soil (pH 8.8) at 25° C. and 35° C. All samples were treated with the fertiliser $(NH_4)_2SO_4$ at a rate of 100 mg N $kg^{-1}$ on day 0. Values presented are means (n=3); errors are standard errors of the mean. Inhibition of nitrification is indicated by slow $NO_x^-$—N production rates.

The calculated $NO_x^-$—N production rates shown in FIG. 2 indicate that incubation at 25° C. led to lower $NO_x^-$—N accumulation in all treatments compared with those at 35° C., except for Compounds 2 and 14, where the $NO_x^-$—N accumulation was lower at the elevated temperature. The rate of $NO_x^-$—N accumulation in soil treated with Compound 13 was the same at both temperatures (2.8 mg $NO_x^-$—N/kg soil/day), whilst treatment with H-DMPP showed the greatest increase in production rate at the higher test temperature.

Dahlen Soil

Figure 3:
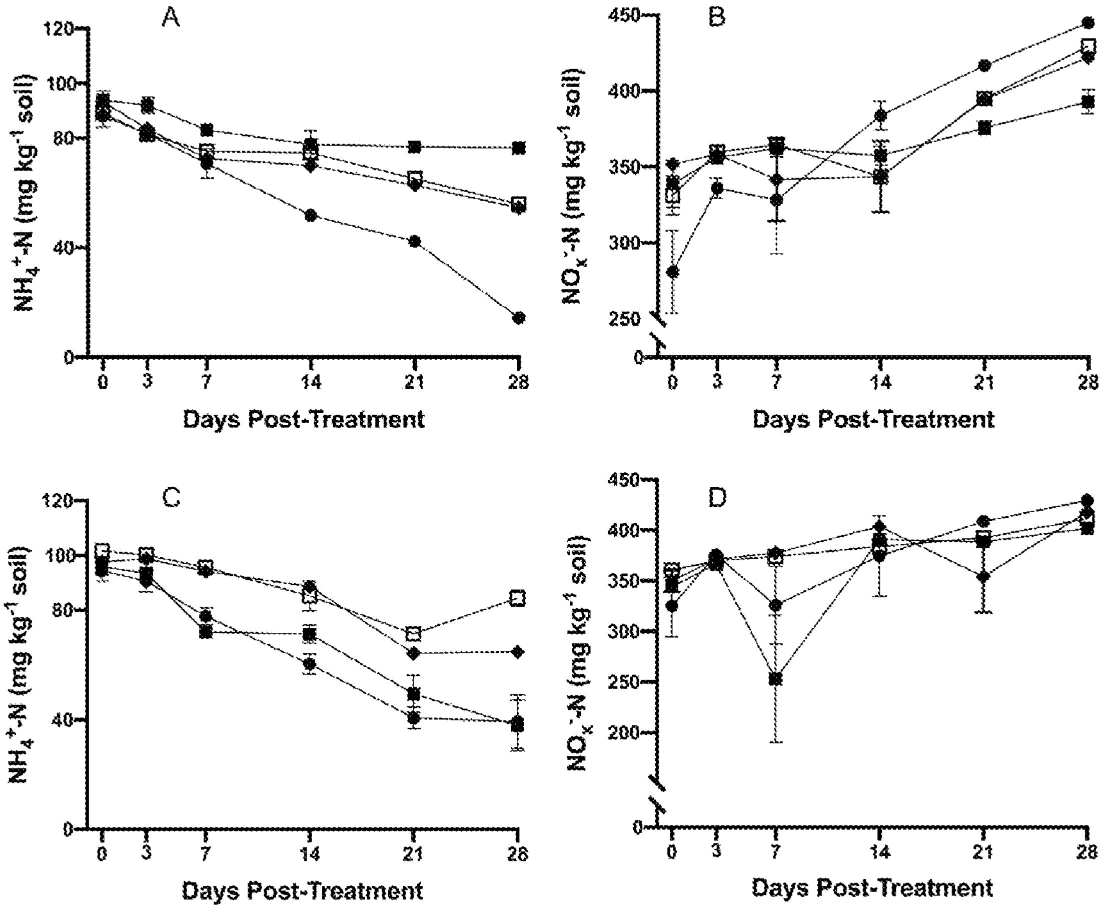
FIG. 3 illustrates the measured $NH_4^+$—N (A, C) and $NO_x^-$—N (B, D) concentrations of Dahlen soil incubated at 25° C. (A, B) and 35° C. (C, D) following treatment with: $(NH_4)_2SO_4$ [●], $(NH_4)_2SO_4$+H-DMPP [■], $(NH_4)_2SO_4$+13 [♦], $(NH_4)_2SO_4$+16 [□]. Inhibition of nitrification is indicated by a slow decrease of $NH_4^+$—N and slow increase of $NO_x^-$—N.

In the Dahlen soil, all of Compounds 2, 13, 16 and 17 performed statistically better (P<0.001) at retaining $NH_4^+$—N than the uninhibited control treatment and DMPP after 28 days at 25° C. The results from these tests are shown in FIG. 3 and Table 4. At the elevated temperature of 35° C., all four triazoles out-performed H-DMPP at slowing the rate of ammonia nitrification. The considerably large error for the $NO_x^-$—N measurements shown in FIGS. 3B and 3D is likely due to the fact that this soil was particularly rich in $NO_3^-$ ($NO_3^-$—N: 270 mg $kg^{-1}$), compared with the other soils (Horsham $NO_3^-$—N: 7.2 mg $kg^{-1}$; Terang $NO_3^-$—N: 27 mg $kg^{-1}$) prior to commencing testing.

Incubation studies in this soil at 35° C. with DMPP and Compounds 2, 13, 16 and 17 (data are included in Table 4) revealed that DMPP performed significantly poorer at the higher temperature, while all of Compounds 2, 13, 16 and 17 performed statistically better (P<0.001) at retaining $NH_4^+$ than both the DMPP treatment and control treatment after 28 days, with ammonia consumption ranging from 17% (16) to 38% (17). The measured concentrations of $NH_4^+$—N and $NO_x^-$—N for these compounds are shown in FIGS. 3C and 3D.

Figure 4:
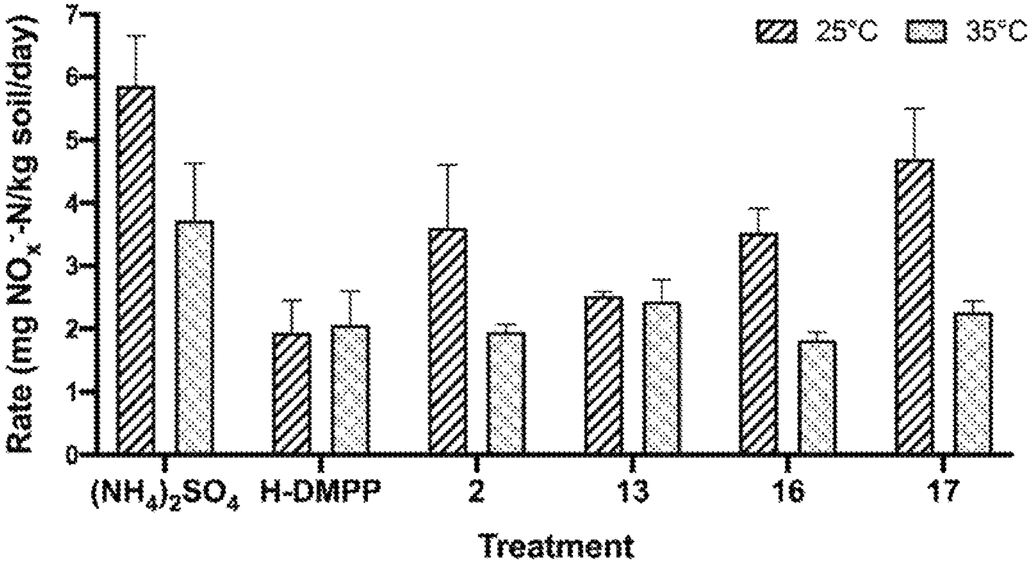
FIG. 4 illustrates the calculated $NO_x^-$—N production rates (mg $NO_x^-$—N/kg soil/day) after 28-day incubations in the Dahlen soil (pH 7.3) at 25° C. and 35° C. All samples were treated with the fertiliser $(NH_4)_2SO_4$ at a rate of 100 mg N $kg^{-1}$ on day 0. Values presented are means (n=3); errors are standard errors of the mean. Inhibition of nitrification is indicated by slow $NO_x^-$—N production rates.

The rate of $NO_x^-$—N accumulation in the soil over the 28-day incubation period is shown in FIG. 4. Thus, incubation at 25° C. resulted in higher $NO_x^-$—N accumulation for all treatments compared with those performed at 35° C., except for DMPP. Treatment with 16 at 35° C. resulted in the lowest accumulation rate (1.8 mg $NO_x^-$—N/kg soil/day), whereas the highest accumulation rate in a treated soil occurred for treatment with Compound 17 at 25° C. (4.7 mg $NO_x^-$—N/kg soil/day). Interestingly, the accumulation rate dropped to 2.4 mg $NO_x^-$—N/kg soil/day for Compound 17 at 35° C., which is the largest reduction in the accumulation rate for all inhibitors tested in this series. On the other hand, the rate of $NO_x^-$—N accumulation in soil treated with Compound 13 was least affected by the temperature change (2.5 vs 2.4 mg $NO_x^-$—N/kg soil/day, at 25° C. and 35° C., respectively), mirroring the seemingly temperature-independent behaviour observed in the Horsham soil for this Compound.

TABLE 4

Ammonia nitrified (%) during a 28-day incubation at either 25° C. or 35° C. in Dahlen soil (pH 7.3). Emboldened values indicate nitrification rates lower than those observed in the control treatment ($(NH_4)_2SO_4$), correlating positively to inhibitor activity. Errors stated are standard errors of the mean, n = 3.

| Test Temp (° C.) | Treatment | Nitrified $NH_4^+$—N (%) Day 3 | Day 7 | Day 14 | Day 21 | Day 28 |
|---|---|---|---|---|---|---|
| 25 | $(NH_4)_2SO_4$ | 7.3 ± 3.1 | 19.6 ± 15.2 | 41.1 ± 10.0 | 52.0 ± 9.5 | 83.6 ± 13.3 |
| | $(NH_4)_2SO_4$ + 2 | 7.5 ± 5.2 | 21.2 ± 12.2 | 20.3 ± 21.6 | 32.9 ± 18.4 | 37.6 ± 11.0 |
| | $(NH_4)_2SO_4$ + 13 | 10.6 ± 3.7 | 22.2 ± 50.2 | 24.9 ± 59.3 | 32.6 ± 2.4 | 41.5 ± 1.2 |
| | $(NH_4)_2SO_4$ + 16 | 8.8 ± 3.3 | 15.6 ± 5.0 | 16.4 ± 28.7 | 26.9 ± 4.6 | 37.3 ± 4.4 |
| | $(NH_4)_2SO_4$ + 17 | 3.0 ± 1.3 | 10.4 ± 3.6 | 12.1 ± 3.2 | 22.2 ± 5.0 | 36.4 ± 6.8 |
| | $(NH_4)_2SO_4$ + H-DMPP | 2.1 ± 2.8 | 11.7 ± 6.7 | 17.3 ± 12.7 | 18.2 ± 6.6 | 18.6 ± 4.9 |
| 35 | $(NH_4)_2SO_4$ | 4.0 ± 4.7 | 17.5 ± 4.3 | 36.1 ± 4.7 | 56.9 ± 5.0 | 58.3 ± 9.3 |
| | $(NH_4)_2SO_4$ + 2 | 1.7 ± 3.3 | −1.3 ± 1.9 | 2.0 ± 2.4 | 29.6 ± 3.6 | 22.4 ± 1.5 |
| | $(NH_4)_2SO_4$ + 13 | −1.2 ± 1.1 | 3.5 ± 1.3 | 9.2 ± 1.1 | 34.2 ± 2.4 | 33.6 ± 1.3 |

TABLE 4-continued

Ammonia nitrified (%) during a 28-day incubation at either 25° C. or 35° C. in Dahlen soil (pH 7.3). Emboldened values indicate nitrification rates lower than those observed in the control treatment ($(NH_4)_2SO_4$), correlating positively to inhibitor activity. Errors stated are standard errors of the mean, n = 3.

| Test Temp (° C.) | Treatment | Nitrified $NH_4^+$—N (%) Day 3 | Day 7 | Day 14 | Day 21 | Day 28 |
|---|---|---|---|---|---|---|
| | $(NH_4)_2SO_4$ + 16 | 1.5 ± 1.4 | 6.0 ± 1.5 | 16.1 ± 4.5 | 29.8 ± 1.2 | 16.9 ± 2.6 |
| | $(NH_4)_2SO_4$ + 17 | 6.3 ± 2.2 | 8.8 ± 1.9 | 17.7 ± 2.6 | 38.0 ± 2.8 | 37.6 ± 3.1 |
| | $(NH_4)_2SO_4$ + H-DMPP | 2.4 ± 3.0 | 24.8 ± 2.7 | 25.6 ± 3.8 | 48.3 ± 6.4 | 60.5 ± 8.4 |

Figure 5:
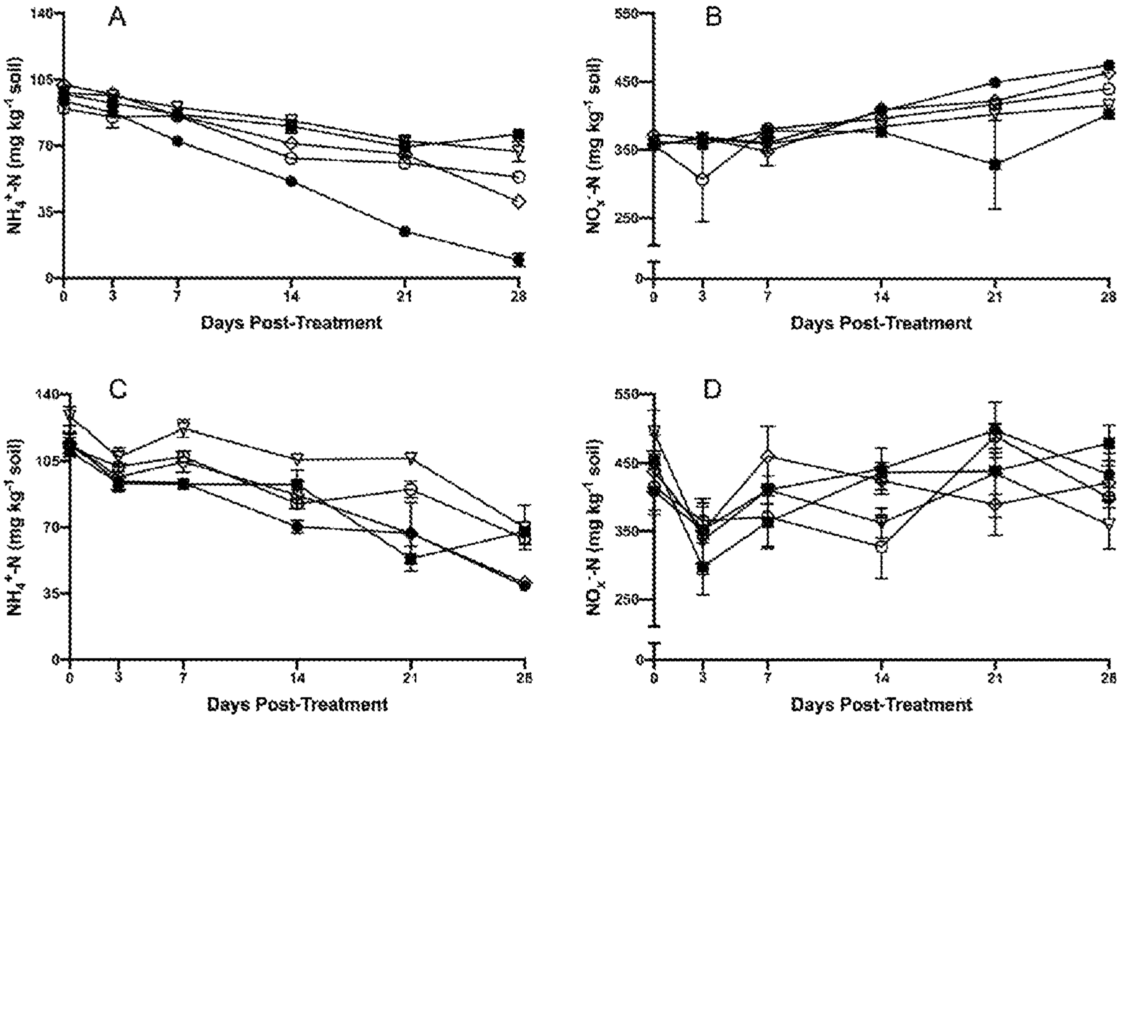
FIG. 5 illustrates the measured $NH_4^+$—N (A, C) and $NO_x$—N (B, D) concentrations of Dahlen soil incubated at 25° C. (A, B) and 35° C. (C, D) following treatment with: $(NH_4)_2SO_4$ [●], $(NH_4)_2SO_4$+H-DMPP [■], $(NH_4)_2SO_4$+18 [○], $(NH_4)_2SO_4$+20 [∇], $(NH_4)_2SO_4$+23 [◇]. Inhibition of nitrification is indicated by a slow decrease of $NH_4^+$—N and slow increase of $NO_x^-$—N.

Further comparative tests were conducted in Dahlen soil for Compounds 18, 20 and 23, against H-DMPP at both 25° C. and 35° C. The results of these tests are shown in FIG. 5 and Table 5 below. Again, it should be noted that the considerably large error for the $NO_x^-$—N measurements shown in FIGS. 5B and 5D is likely due to the fact that this soil was particularly rich in $NO_3^-$ (see above).

South Johnstone Soil

Figure 6:
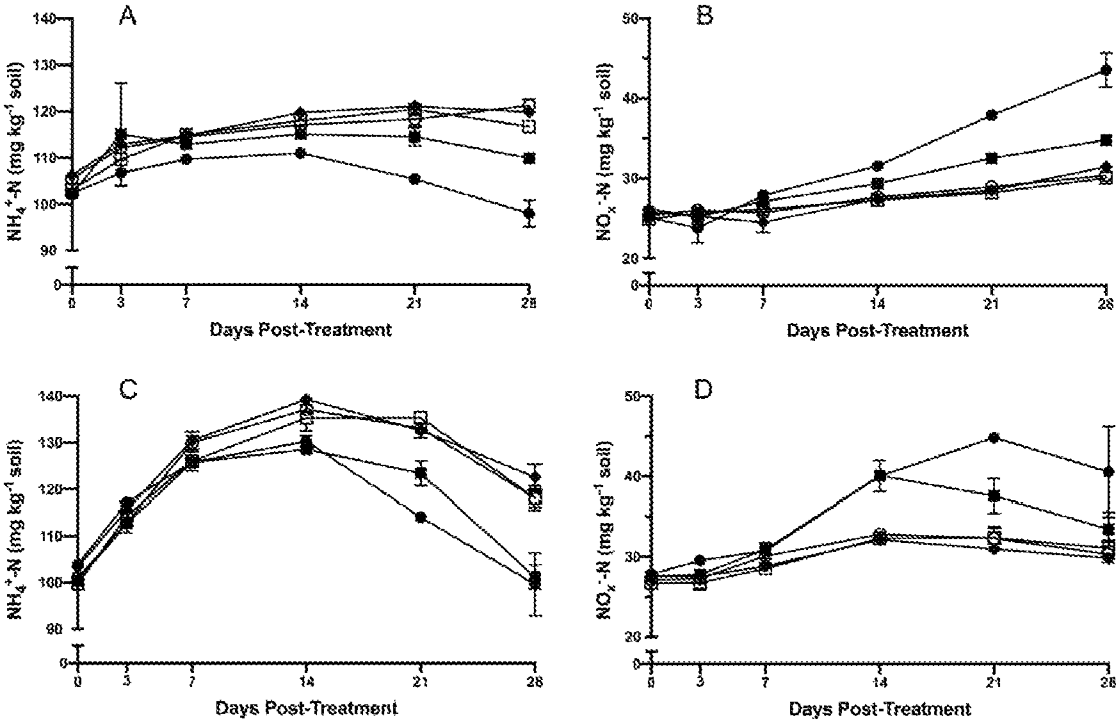
FIG. 6 illustrates the measured $NH_4^+$—N (A, C) and $NO_x$—N (B, D) concentrations of South Johnstone soil incubated at 25° C. (A, B) and 35° C. (C, D) following treatment with: $(NH_4)_2SO_4$ [●], $(NH_4)_2SO_4$+H-DMPP [■], $(NH_4)_2SO_4$+3 [♦], $(NH_4)_2SO_4$+16 [□], $(NH_4)_2SO_4$+18 [○]. Inhibition of nitrification is indicated by a slow decrease of $NH_4^+$—N and slow increase of $NO_x^-$—N.

The behaviour of the detected $NH_4^+$—N and $NO_x^-$—N concentrations differed in South Johnstone soil compared with the other soils studied. The increasing $NH_4^+$—N concentrations observed over the first 14 days indicates that mineralisation of nitrogen is occurring in the soil. The test at 35° C. included a water-only control treatment in addition to the $(NH_4)_2SO_4$-treated control, which indicated that mineralisation occurred in the soil regardless of treatment, and was stimulated by the addition of the nitrogen-based fertiliser. This 'complication' makes assessment of the impact of the tested compounds on the nitrification process more difficult, because only from day 14 onwards the $NH_4^+$—N begins to show net consumption instead of net growth (from the mineralisation). The amount of ammonia lost compared to the amount detected on day 0 for selected treatments is displayed in Table 6 for tests at both 25° C. and 35° C., whilst FIG. 6 illustrates the measured amounts of $NH_4^+$—N and $NO_x^-$—N. For almost all entries, the percentages are negative, which indicates the [$NH_4^+$—N] at that time point remains higher than what was detected on day 0 (due to the mineralisation process). From day 14 onwards, larger negative percentages indicate which treatments were more effective at preventing [$NH_4^+$—N] losses.

At 25° C., all treatments performed significantly better than the $(NH_4)_2SO_4$ control treatment at both retaining $NH_4^+$—N and slowing $NO_x^-$—N growth on days 21 and 28 (see FIG. 6). Of the treatments, Compound 19 and DMPP were the least effective (although still significantly better than the control treatment). Compared to treatment with

TABLE 5

Ammonia nitrified (%) during a 28-day incubation at either 25° C. or 35° C. in Dahlen soil (pH 7.3). Emboldened values indicate nitrification rates lower than those observed in the control treatment ($(NH_4)_2SO_4$), correlating positively to inhibitor activity. Errors stated are standard errors of the mean, n = 3.

| Test Temp (° C.) | Treatment | Nitrified $NH_4^+$—N (%) Day 3 | Day 7 | Day 14 | Day 21 | Day 28 |
|---|---|---|---|---|---|---|
| 25 | $(NH_4)_2SO_4$ | 6.4 ± 0.6 | 22.5 ± 1.1 | 45.2 ± 2.4 | 73.6 ± 0.9 | 89.7 ± 3.0 |
| | $(NH_4)_2SO_4$ + 18 | 5.1 ± 5.3 | 4.4 ± 1.1 | 29.4 ± 2.4 | 32.1 ± 2.3 | 40.5 ± 1.5 |
| | $(NH_4)_2SO_4$ + 20 | 1.9 ± 1.3 | 8.0 ± 0.6 | 15.2 ± 1.2 | 26.0 ± 2.1 | 31.8 ± 4.5 |
| | $(NH_4)_2SO_4$ + 23 | 4.8 ± 2.9 | 15.7 ± 1.5 | 30.3 ± 0.8 | 35.9 ± 1.2 | 60.5 ± 1.0 |
| | $(NH_4)_2SO_4$ + H-DMPP | 4.9 ± 3.1 | 11.0 ± 3.2 | 17.4 ± 4.2 | 28.7 ± 5.2 | 21.8 ± 3.3 |
| 35 | $(NH_4)_2SO_4$ | 17.5 ± 5.3 | 18.2 ± 3.6 | 38.4 ± 4.5 | 41.4 ± 12.2 | 65.9 ± 4.7 |
| | $(NH_4)_2SO_4$ + 18 | 9.0 ± 4.3 | 4.5 ± 4.3 | 26.7 ± 3.9 | 19.8 ± 5.0 | 43.0 ± 4.7 |
| | $(NH_4)_2SO_4$ + 20 | 16.6 ± 4.5 | 5.0 ± 4.3 | 17.7 ± 3.8 | 17.1 ± 3.6 | 45.6 ± 8.3 |
| | $(NH_4)_2SO_4$ + 23 | 15.6 ± 6.4 | 8.8 ± 5.6 | 24.0 ± 6.7 | 41.7 ± 4.7 | 64.6 ± 4.9 |
| | $(NH_4)_2SO_4$ + H-DMPP | 15.3 ± 2.9 | 15.8 ± 2.5 | 16.0 ± 6.0 | 51.5 ± 5.4 | 38.5 ± 2.9 |

At 25° C., Compounds 18 and 23 performed statistically better at retaining $NH_4^+$—N levels in the soil by day 28 compared to both the fertilised control and DMPP ($P<0.001$). Compound 20 performed statistically better than the fertilised control ($P<0.001$). However, this effectiveness was not reflected in reductions in $NO_x^-$—N concentrations, where none of the treatments showed significant effectiveness on day 28 compared to the control treatment or DMPP, respectively.

At 35° C., the trends in $NH_4^+$—N and $NO_x^-$—N concentrations were less linear than those observed at 25° C., particularly for the $NO_x^-$—N data. Compounds 18 and 20 and DMPP were the only treatments to remain highly effective at retaining $NH_4^+$—N in the soil compared to the $(NH_4)_2SO_4$-treated control by day 28 (18: $P<0.01$, 20: $P<0.001$). However, the large decrease in $NH_4^+$—N concentration observed on day 21 for the DMPP treatment, corresponding to an essential loss of inhibitory activity (52% nitrified ammonia compared to only 41% for the control, see Table 5) was not reflected by treatments with Compounds 18 and 20. With regards to the $NO_x^-$—N data, all NIs except for DMPP showed lower $NO_x^-$—N concentrations than the control on day 28, however not to a statistically significant extent.

DMPP, Compounds 3 and 18 both showed statistically higher effectiveness based on higher $NH_4^+$—N and lower $NO_x^-$—N concentrations on day 28 (3: P<0.05 and <0.01, respectively; 18: P<0.01 and <0.001, respectively).

TABLE 6

Ammonia nitrified (%) during a 28-day incubation, conducted in South Johnstone soil (pH 5.0). Nitrification values calculated from ammonia levels detected in samples at each time point. All samples were treated with fertiliser $(NH_4)_2SO_4$ at a rate of 100 mg N $kg^{-1}$.
Emboldened values indicate nitrification rates lower than those observed in the control treatment ($(NH_4)_2SO_4$), correlating positively to inhibitor activity.
Values reported as means (n = 3); errors reported are standard errors of the mean.

| Test Temp (° C.) | Treatment | Nitrified $NH_4^+$—N (%) Day 3 | Day 7 | Day 14 | Day 21 | Day 28 |
|---|---|---|---|---|---|---|
| 25 | $(NH_4)_2SO_4$ | −4.3 ± 2.3 | −7.2 ± 0.7 | −8.5 ± 0.8 | −3.0 ± 0.8 | 4.2 ± 2.4 |
| | $(NH_4)_2SO_4$ + 3 | −6.3 ± 0.7 | −7.9 ± 0.9 | −12.7 ± 0.7 | −13.9 ± 0.9 | −12.8 ± 0.8 |
| | $(NH_4)_2SO_4$ + 16 | −6.3 ± 0.8 | −11.5 ± 0.8 | −14.4 ± 0.7 | −16.8 ± 1.2 | −13.2 ± 0.7 |
| | $(NH_4)_2SO_4$ + 18 | −6.2 ± 0.9 | −8.5 ± 1.0 | −11.0 ± 1.0 | −12.1 ± 1.4 | −14.9 ± 1.4 |
| | $(NH_4)_2SO_4$ + H-DMPP | −12.5 ± 8.8 | −10.3 ± 0.7 | −12.5 ± 0.6 | −12.0 ± 1.6 | −7.5 ± 0.5 |
| 35 | $(NH_4)_2SO_4$ | −12.9 ± 0.6 | −21.2 ± 0.9 | −25.4 ± 1.1 | −9.8 ± 0.72 | 4.1 ± 5.3 |
| | $(NH_4)_2SO_4$ + 3 | −11.8 ± 1.5 | −26.2 ± 1.5 | −34.8 ± 0.6 | −28.3 ± 1.4 | −18.6 ± 2.3 |
| | $(NH_4)_2SO_4$ + 16 | −14.7 ± 1.9 | −26.3 ± 1.7 | −35.7 ± 2.4 | −35.7 ± 0.6 | −18.4 ± 2.3 |
| | $(NH_4)_2SO_4$ + 18 | −11.7 ± 2.0 | −28.7 ± 1.5 | −35.8 ± 1.3 | −31.7 ± 1.1 | −16.9 ± 1.8 |
| | $(NH_4)_2SO_4$ + H-DMPP | −12.3 ± 1.2 | −25.3 ± 0.9 | −28.1 ± 1.3 | −23.0 ± 2.3 | −0.90 ± 2.3 |

At 35° C., only the subset of Compounds 3, 16 and 18 performed statistically better than the fertilised control at both retaining $NH_4^+$—N and slowing $NO_x^-$—N growth on day 28 (P<0.001). At this temperature Compounds 3, 16 and 18 also performed statistically better than DMPP at retaining $NH_4^+$—N(P<0.001 for 3 and 16, P<0.05 for 18).

2.2. Leaching Studies for DMP and 16

Leachability of soil nitrification inhibitors is an important consideration, due to the potential cascading health consequences that may arise if chemical inhibitors move through the soil profile and enter ground water supplies in high concentrations. It is also an important consideration for the effectiveness of the inhibitor, as high mobility in soils may lead to spatial separation between the inhibitor, $NH_4^+$ ions and the microorganisms involved in the nitrification process, leading to reduced field effectiveness.

Traditional soil leaching columns are both material and time intensive and could not be undertaken due to limited access to the soils of interest. Therefore, a soil thin-layer chromatography (TLC) technique was developed by modifying a method that has previously been described for the investigation of pesticide leaching behaviour (Helling, C. S., Turner, B. C, *Science* 1968, 162, 562-563). The advantage of the TLC technique is that data can be provided very quickly requiring only small amounts of soil and substrate.

2.2.1. General Soil Thin Layer Chromatography (TLC) Plate Preparation

TLC plates were prepared based on methods described in the literature (Helling, C. S., Turner, B. C, *Science* 1968, 162, 562-563; Mohammad, A., Jabeen, N., *JPC—Journal of Planar Chromatography—Modern TLC* 2003, 16, 137-143). Masking tape (3 layers, ~450 m total thickness) was used to outline three columns (4 cm W×12 cm H) on a glass TLC plate (20×20 cm). A slurry of freshly ground soil in distilled $H_2O$ (~2:3 m/v) was then poured onto the prepared plate and spread evenly using a glass rod. Once even, the plate was dried overnight in an oven at 35° C. Careful removal of the masking tape afforded the TLC plate ready for sample application.

2.2.2. Leaching Studies of DMP and Compound 16

Samples of DMP (the active core of DMPP) or Compound 16 (~1 mg) dissolved in acetone (100 μL) were pipetted in a straight line across the soil, 2 cm above the base of the plate. Application band thickness was kept under 0.5 cm. After 30 mins of drying time, the TLC plate was developed inside a glass developing chamber with distilled $H_2O$ (depth of 0.5 cm) until the solvent front reached the top of the soil (~1 hr). If the solvent front failed to move through the three adjacent soil channels at the same rate, the plate was removed once the solvent reached the top of one channel, with any dry soil in the remaining channels carefully scraped away to mark the height of the solvent front. The plate was then allowed to air dry overnight.

Once dry, the plate was divided into six horizontal bands corresponding to $R_f$ values of: (1) <0.05 (baseline), (2) 0.05 to 0.25, (3) 0.25 to 0.45, (4) 0.45 to 0.65, (5) 0.65 to 0.85, and (6) 0.85 to 1. In sequence, soil in each band was carefully scraped off the glass backing and collected in vials. Special care was taken to avoid cross-contamination between soil of different bands, and the separate channels.

2.2.3. Extraction and Analysis of DMP and Compound 16

Individual soil bands collected from the TLC plate were extracted as follows:

1. Addition of an aqueous solution of $CaCl_2/MgSO_4$ (0.01M and 0.45M respectively, 2 mL).
2. Sonication for 5 minutes then manual shaking for 30 seconds.
3. Addition of methyl-tert-butyl ether (MTBE, 2 mL) then manual shaking for 30 seconds.
4. Sonication for 10 minutes then manual shaking for 30 seconds.
5. Rested until soil began to settle, then frozen overnight at −20° C.
6. After partial defrosting, the ethereal extract was filtered through nylon syringe filters (FilterBio®, 13 mm diameter, 0.45 μm pore size).

The filtered ethereal extracts (450 μL) were spiked with 50 μL of a standard solution of either cyclododecanone in MTBE (1.97 mg/mL, for DMP-treated samples) or cyclooctanone in MTBE (6.37 mg/mL, for 16-treated samples). Samples were then directly analysed by GC-MS (method: 70° C. for 5 mins, then ramp 10° C./min to 250° C., hold at 250° C. for 17 mins [total run time=40 minutes]) to analyse the presence or absence of the inhibitor in each soil band.

2.2.4. Leached Inhibitor Calculations

GC-MS peak areas calculated for the standards cyclooctanone ($R_t$=9.1 mins) and cyclododecanone ($R_t$=15.8 mins) were compared to those calculated for Compound 16 ($R_t$=13.9 mins) and DMP ($R_t$=7.6 mins) respectively, for each soil sample extract where inhibitor was detected as follows:

$$Ratio_{Area} = \frac{\text{Peak } Area_{inhibitor}}{\text{Peak } Area_{standard}}$$

then for samples from a single TLC channel;

$$\%\text{ Detected inhibitor (per } R_f \text{ band)} = \frac{Ratio_{Area}(\text{specific } R_f \text{ band})}{\text{Sum of } Ratio_{Area} \text{ of all } R_f \text{ bands}} \times 100$$

As each treatment was run in triplicate, mean values are reported for detected inhibitor percentages for each $R_f$ band, with errors presented as the standard deviation.

TABLE 7

Results from soil Thin-Layer Chromatography (TLC) to assess the leaching potential of inhibitors DMP and Compound 16 in two soils.

| | Detected Inhibitor (%)[a] | | | |
|---|---|---|---|---|
| | 16[b] | | DMP[c] | |
| $R_f$ | Dahlen | South Johnstone | Dahlen | South Johnstone |
| <0.05 | n.d. | n.d. | n.d. | n.d. |
| 0.05-0.25 | 3 ± 4 | 1 ± 1 | n.d. | n.d. |
| 0.25-0.45 | 58 ± 14 | 5 ± 6 | n.d. | 2 ± 2 |
| 0.45-0.65 | 38 ± 16 | 34 ± 5 | 0.1 ± 0.2 | 56 ± 12 |
| 0.65-0.85 | 1 ± 1 | 49 ± 9 | 72 ± 16 | 42 ± 13 |
| 0.85-1 | n.d. | 11 ± 3 | 28 ± 16 | n.d. |

[a]Means of three replicates, error presented is the standard deviation.
[b]Values were calculated compared to internal standard cyclooctanone.
[c]Values were calculated compared to internal standard cyclododecanone.
Not detected = n.d.

2.2.5. Leaching Studies of DCD

Samples of the DCD (~1 mg) dissolved in methanol (300 μL) were pipetted in a straight line across the soil, 2 cm above the base of the plate. Application band thickness was kept under 0.5 cm. After 30 mins of drying time, the TLC plate was developed inside a glass developing chamber in distilled $H_2O$ (depth of 0.5 cm) until the solvent front reached the top of the soil (~1 hr). If the solvent front failed to move through the three adjacent soil channels at the same rate, the plate was removed once the solvent reached the top of the soil in one channel, with any dry soil in the remaining channels carefully scraped away to mark the height of the solvent front. The plate was then allowed to air dry overnight.

Once dry, the plate was divided into six horizontal bands corresponding to $R_f$ values of: (1) <0.05 (baseline), (2) 0.05 to 0.25, (3) 0.25 to 0.45, (4) 0.45 to 0.65, (5) 0.65 to 0.85, and (6) 0.85 to 1. In sequence, soil in each band was carefully scraped off the glass backing and collected in vials. Special care was taken to avoid cross-contamination between soil of different bands, and the separate channels.

2.2.6. Extraction and Analysis of DCD

Individual soil bands collected from the TLC plate were extracted as follows:

1. Addition of methanol (2 mL).
2. Manual shaking for 30 seconds following sonication for 15 minutes.
3. Once soil began to settle, the methanolic extract was filtered through nylon syringe filters (FilterBio®, 13 mm diameter, 0.45 μm pore size).
4. 300 μL of the methanolic extracts were evaporated under nitrogen flow, and then the residues was taken up in ultrapure acetonitrile (1 mL).
5. Acetonitrile solutions were filtered through PVDF syringe filters (Millex®, 33 mm diameter, 0.22 μm pore size).

The filtered acetonitrile extracts (10 μL injection) were then directly analysed by HPLC (1260 Infinity II Preparative LC system with a C18 column, Agilent) to detect the presence or absence of DCD in each soil band at 214 nm. The HPLC method used was as follows:

Solvent A: 0.1% formic acid in $H_2O$

Solvent B: 0.1% formic acid in acetonitrile

Ramp from 100% A to 100% B over ten mins. Hold at 100% B for two mins then return to 100% A in 10 secs, for a 2-minute wash at 100% A. Total sample run time=15 mins.

2.2.7. Results

Figure 7:
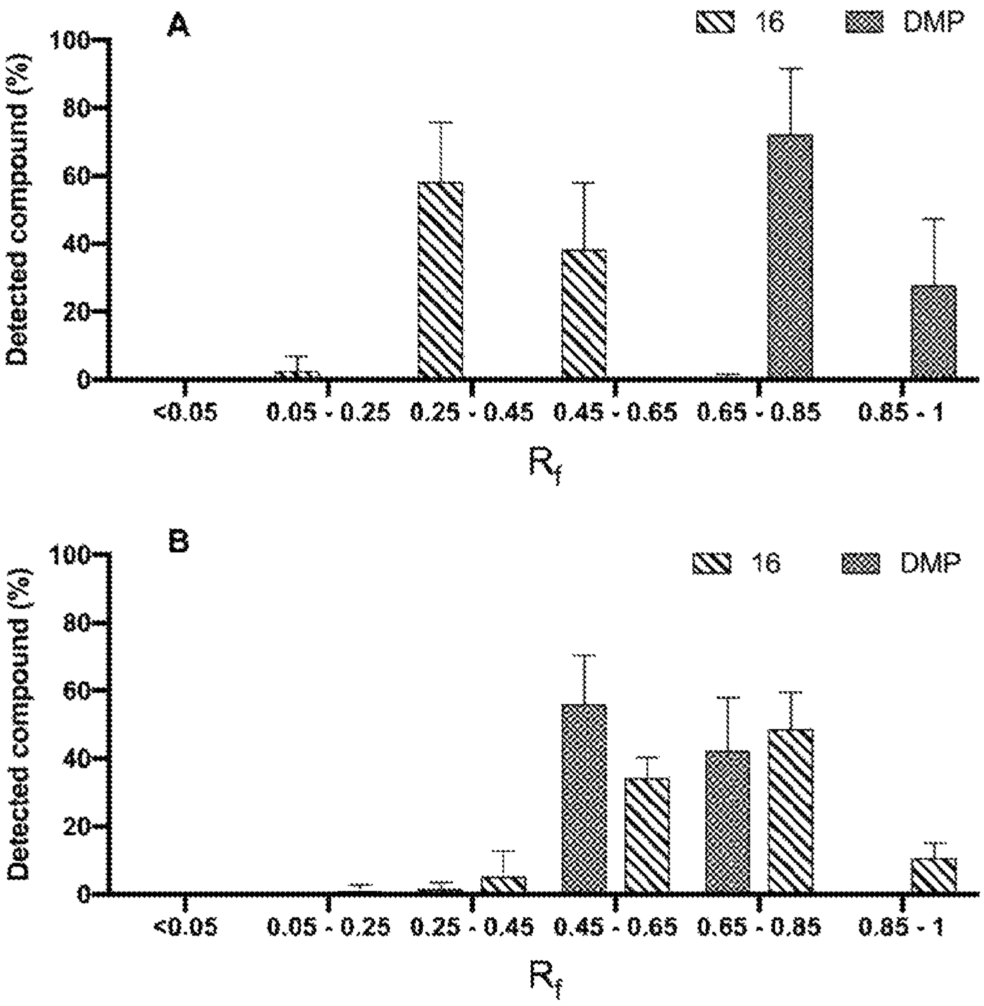
FIG. 7 illustrates the results of soil TLC leaching of inhibitor compounds DMP and Compound 16 in Dahlen soil (A) or South Johnstone soil (B). Higher $R_f$ values indicate higher degrees of leachability through the soil profile.

The retention factor ($R_f$) is used to measure the movement of compounds through the soil using the TLC method, with a high $R_f$-value close to 1 indicating high mobility through the soil. In the neutral Dahlen soil, Compound 16 showed reduced mobility compared to DMP, with the majority of the triazole detected in the $R_f$ range 0.25-0.45, versus 0.65-0.85 for DMP (see FIG. 7). For the acidic South Johnstone soil, DMP was found to leach in a narrower band and to a lesser extent than Compound 16. This may be due to protonation of DMP in lower pH environments. The resulting charged molecule may be adsorbed on the soil particles, therefore reducing leaching. However, since DMP is not the target of this investigation, the underlying process was not explored.

Dicyandiamide (DCD) is a widely used nitrification inhibitor, which, due to its high water solubility, has known leaching concerns. Preliminary results from TLC leaching studies of DCD in both the Dahlen and South Johnstone soils show the largest DCD accumulation in the $R_f$ range 0.65-1. This result contradicts the correlation between protonation ease and reduced mobility, as DCD has multiple protonation sites and would therefore be expected to leach less.

The results from these leaching studies indicate that in neutral soils Compound 16, and by extension other similar small lipophilic triazoles, have lower leachability than DMP and DCD. Acidic soils again seem to be potentially more problematic, however Compound 16 does still appear to show lower-to-similar leaching tendencies to DCD.

The claims defining the invention are as follows:

1. A method for reducing nitrification in soil comprising treating the soil with a compound of Formula (I):

(I)

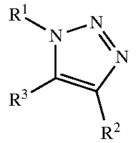

wherein $R^1$ is selected from —$C_1$-$C_{10}$alkyl; —$C_2$-$C_{10}$alkenyl; —$C_2$-$C_{10}$alkynyl; —$C_1$-$C_{10}$alkylC(O)O$R^4$; and —$C_1$-$C_{10}$alkylC(O)NH$R^4$;

$R^2$ is —$C_1$-$C_{10}$alkyl;

$R^3$ is H; and $R^4$ is selected from —$C_1$-$C_4$alkyl, —$C_2$-$C_4$alkenyl and —$C_2$-$C_4$alkynyl;

or agriculturally acceptable salts thereof.

2. A method according to claim 1, wherein the soil is co-treated with a urease inhibitor.

3. A method according to claim 1, wherein the soil is co-treated with a fertiliser.

4. The method according to claim 1, wherein $R^1$ is selected from —$C_1$-$C_4$alkyl —$C_2$-$C_4$alkenyl; —$C_2$-$C_4$alkynyl; —$C_1$-$C_4$alkylC(O)O$R^4$; and —$C_1$-$C_4$alkylC(O)NH$R^4$; and $R^2$ is —$C_1$-$C_4$alkyl.

* * * * *